US008563516B2

(12) United States Patent
Tsunoda et al.

(10) Patent No.: US 8,563,516 B2
(45) Date of Patent: Oct. 22, 2013

(54) FOXP3 PEPTIDE VACCINE

(75) Inventors: Takuya Tsunoda, Kanagawa (JP); Ryuji Osawa, Kanagawa (JP)

(73) Assignee: OncoTherapy Science, Inc., Kanagawa (JP)

( * ) Notice: Subject to any disclaimer, the term of this patent is extended or adjusted under 35 U.S.C. 154(b) by 482 days.

(21) Appl. No.: 12/522,066

(22) PCT Filed: Dec. 26, 2007

(86) PCT No.: PCT/JP2007/001466

§ 371 (c)(1),
(2), (4) Date: Nov. 30, 2009

(87) PCT Pub. No.: WO2008/081581

PCT Pub. Date: Jul. 10, 2008

(65) Prior Publication Data

US 2010/0092501 A1 Apr. 15, 2010

Related U.S. Application Data

(60) Provisional application No. 60/896,472, filed on Mar. 22, 2007, provisional application No. 60/878,615, filed on Jan. 3, 2007.

(51) Int. Cl.
*A61P 35/00* (2006.01)

(52) U.S. Cl.
USPC .................................... 514/19.3; 424/185.1

(58) Field of Classification Search
None
See application file for complete search history.

(56) References Cited

U.S. PATENT DOCUMENTS

| | | | | |
|---|---|---|---|---|
| 7,514,084 B2 * | 4/2009 | Tahara et al. | .............. | 424/185.1 |
| 2003/0170648 A1 | 9/2003 | Khattri et al. | | |

FOREIGN PATENT DOCUMENTS

| | | | |
|---|---|---|---|
| EP | 1 548 032 A1 | 6/2005 |
| JP | 2006-052216 A | 2/2006 |
| RU | 2129439 C1 | 4/1999 |
| WO | 93/01831 A1 | 2/1993 |
| WO | WO 2004/024766 A1 | 3/2004 |
| WO | 2006/013336 A1 | 2/2006 |
| WO | WO 2006/077941 A1 | 7/2006 |

OTHER PUBLICATIONS

Janeway et al., Immunobiology, Garland Press, 2001, at pp. 117-118.*
Yewdell et al., Annu. Rev. Immunol. 1999. 17:51-88.*
Banham et al., Eur. J. Immunol. 2006. 36: 2832-2836.*
Moudgil et al., Trends in Immunology vol. 26 No. 7 Jul. 2005, pp. 355-359.*
Leggatt et al., The Journal of Immunology, 1998, 161: 4728-4735.*
Xiaoling, G., et al., "Induction of anti B-cell malignance CTL response by subfamily-shared peptides derived from variable domain of immunoglobulin heavy chain," *Cancer Immunol. Immunother.*, vol. 54(11), pp. 1106-1114 (Nov. 2005, Epub May 12, 2005).
Q9BZS1-1 (FOXP3_HUMAN), database http://www.uniprot.org/uniprot/Q9BZS1, 8 pgs. (Last modified Dec. 14, 2011, downloaded Dec. 28, 2011).
BioInformatics and Molecular Analysis Section, "HLA Peptide Binding Predictions," downloaded from http://www-bimas.cit.nih.gov/molbio/hla_bind/, 1 pg. (downloaded Dec. 28, 2011).
Bubenik, J., et al., "Depletion of $T_{reg}$ Cells Augments the Therapeutic Effect of Cancer Vaccines," *Folia Biologica* (*Praha*), vol. 52(6), pp. 202-204 (2006).
Bui, H-H., et al., "Automated generation and evaluation of specific MHC binding predictive tools: ARB matrix applications," *Immunogenetics*, vol. 57(5), pp. 304-314 (Jun. 2005, Epub May 3, 2005).
Gilboa, E., et al., "Targeting immune evasion in cancer immunotherapy," *Proc Amer Assoc Cancer Res.*, vol. 47, p. 1357, Abstract SY04-01 (4 pgs.), (2006).
Komori, H., et al., "Identification of HLA-A2- or HLA-A24-Restricted CTL Epitopes Possibly Useful for Glypican-3-Specific Immunotherapy of Hepatocellular Carcinoma," *Clin Cancer Res*, vol. 12(9), pp. 2689-2697 (May 1, 2006).
Moutaftsi, M., et al., "A consensus epitope prediction approach identifies the breadth of murine $T_{CD8+}$-cell responses to vaccinia virus," *Nat Biotechnol.*, vol. 24(7), pp. 817-819 (Jul. 2006, Epub Jun. 11, 2006).
Nielsen, M., et al., "Reliable prediction of T-cell epitopes using neural networks with novel sequence representations," *Protein Sci.*, vol. 12(5), pp. 1007-1017 (May 2003).
Nakamura, T., et al., "Expression of idoleamine 2, 3-dioxygenase and the recruitment of Foxp3-expressing regulatory T cells in the development and progression of uterine cervical cancer," *Cancer Sci.*, vol. 98(6), pp. 874-881 (Jun. 2007, Epub Apr. 13, 2007).
Peters, B., et al., "Generating quantitative models describing the sequence specificity of biological processes with the stabilized matrix method," *BMC Bioinformatics*, vol. 6: 132, 9 pgs. (May 31, 2005).
Pietersz, G.A., et al., "Design of Peptide-Based Vaccines for Cancer," *Curr Med Chem.*, vol. 13(14), pp. 1591-1607 (2006).
Strausberg, R.L., et al., "Forkhead box P3 [*Homo sapiens*]," NCBI Accession No. AAI13404, 2 pgs. (Jun. 29, 2006).
Ziegler, S., "FOXP3: Of Mice and Men," *Annu Rev Immunol.*, vol. 24, pp. 209-226 (2006).
Gilboa, E., et al., "Cancer immunotherapy with mRNA-transfected dendritic cells," *Immunol. Rev.*, vol. 199, pp. 251-563 (Jun. 2004).
Kondo, A., et al., "Prominent Roles of Secondary Anchor Residues in Peptide Binding to HLA-A24 Human Class I Molecules," *J. Immunol.*, vol. 155(9), pp. 4307-4312 (Nov. 1, 1995).
Kubo, R., et al., "Definition of Specific Peptide Motifs for Four Major HLA-A Alleles," *J. Immunol.*, vol. 152(8), pp. 3913-3924 (Apr. 15, 1994).
Nair, S., et al., "Vaccination against the Forkhead Family Transcription Factor Foxp3 Enhances Tumor Immunity," *Cancer Res.*, vol. 67(1), pp. 371-380 (Jan. 1, 2007).

(Continued)

*Primary Examiner* — Zachary Skelding
(74) *Attorney, Agent, or Firm* — Kilpatrick Townsend & Stockton LLP

(57) ABSTRACT

The present invention provides Foxp3 peptides comprising the amino acid sequence of SEQ ID NOs: 3-5, 7-9, 12, 15-19, 22, 24, 27-30, 37, 67 or 74, and Foxp3 peptides comprising the above-mentioned amino acid sequences in which 1, 2, or several amino acids are substituted or added, and having cytotoxic T cell inducibility, and also provides drugs for regulating regulatory T cells comprising these Foxp3 peptides. The Foxp3 peptides of this invention find use as vaccines.

5 Claims, 10 Drawing Sheets

(56) References Cited

OTHER PUBLICATIONS

Roncador, G., et al., "Analysis of FOXP3 protein expression in human CD4$^+$CD25$^+$ regulatory T cells at the single-cell level," *Eur. J. Immunol.*, vol. 35(6), pp. 1681-1691 (Jun. 2005).

Zaremba, S., et al., "Identification of an Enhancer Agonist Cytotoxic T Lymphocyte Peptide from Human Carcinoembryonic Antigen," *Cancer Research*, vol. 57(20), pp. 4570-4577 (Oct. 15, 1997).

Banham, et al., "Therapeutic targeting of FOXP3-positive regulatory T cells using a FOXP3 peptide vaccine WO2008081581," *Expert Opin Ther Patents*, vol. 19(7), pp. 1023-1028 (2009).

Dionne, et al., "Her-2/*neu* altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 5, 2003).

Falk, et al., "Allele-specific motifs revealed by sequencing of self-peptide eluted from MHC molecules," *Nature*, vol. 351(6324), pp. 290-296 (May 23, 1991).

Hoffmann, et al., "The Ability of Variant Peptides to Reverse the Nonresponsiveness of T Lymphocytes to the Wild-Type Sequence $p53_{264-272}$Epitope," *J Immunol.*, vol. 168(3), pp. 1338-1347 (Feb. 1, 2002).

Rammensee, et al., "MHC ligands and peptide motifs: first listing," *Immunogenetics*, vol. 41(4), pp. 178-228 (1995).

* cited by examiner

Fig. 1
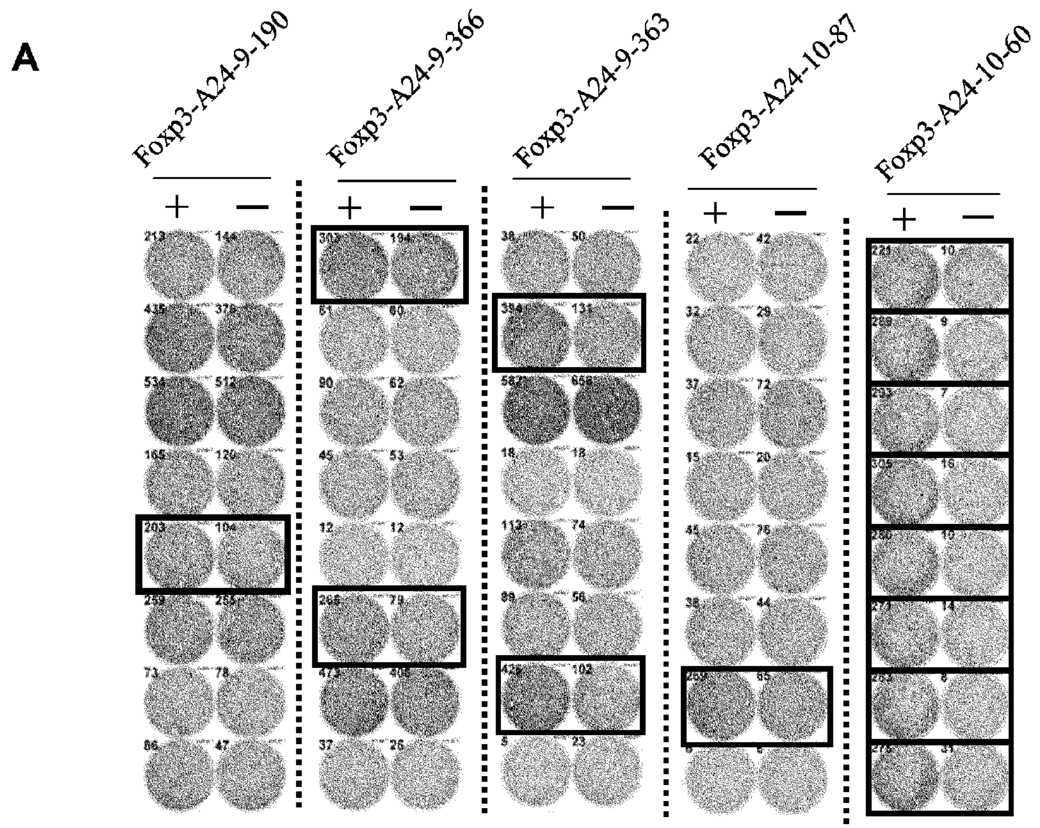
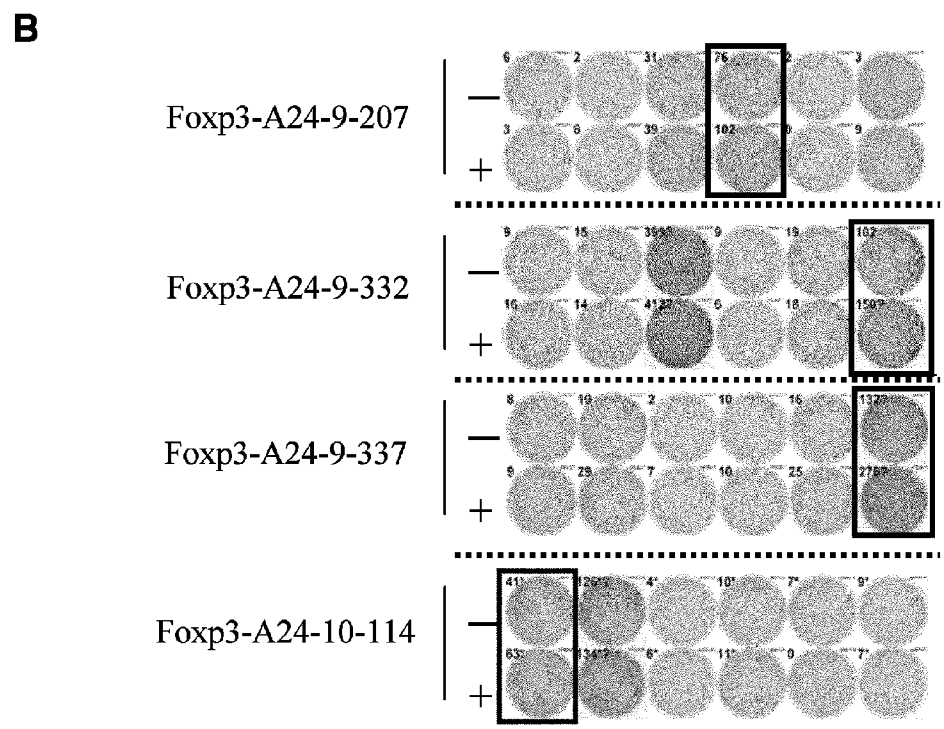

Fig. 2A-B
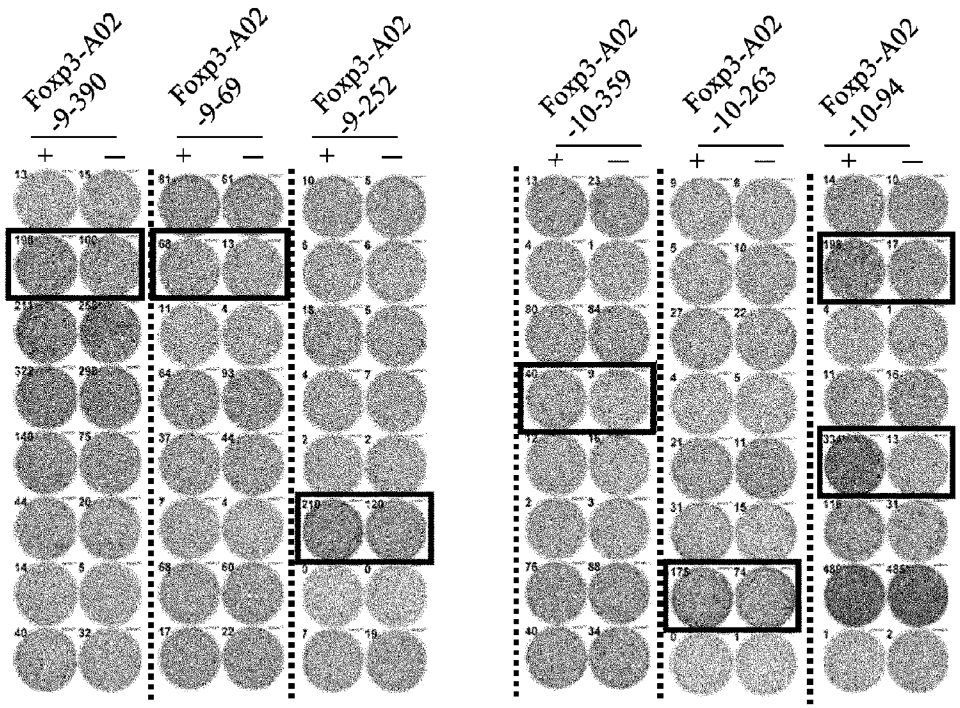
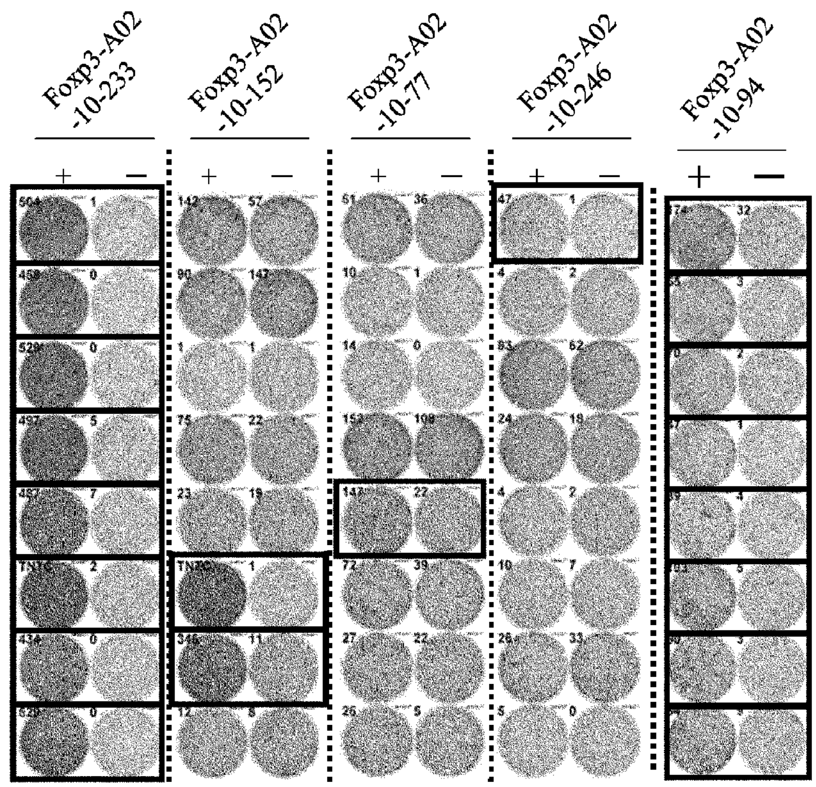

Fig. 2C
C
Foxp3-A2-9-390
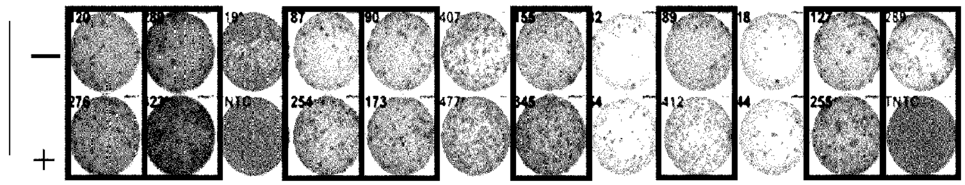
Foxp3-A2-9-304
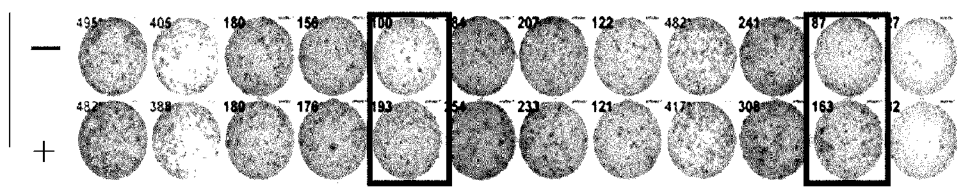
Foxp3-A2-9-68
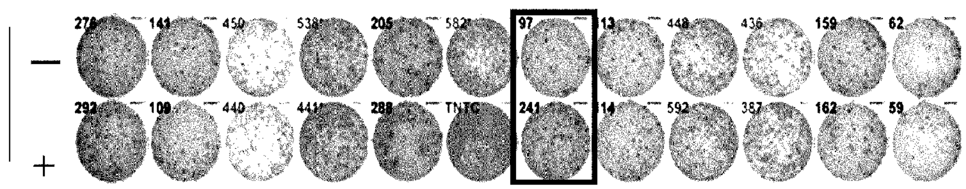
Foxp3-A2-9-252
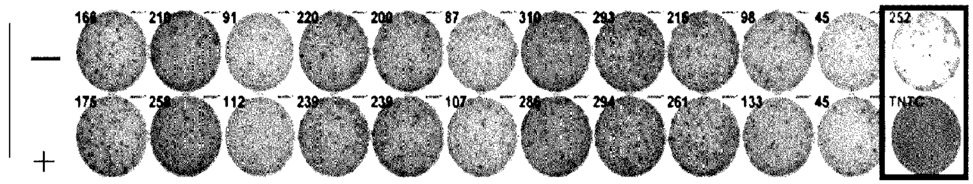

Fig. 3A-D
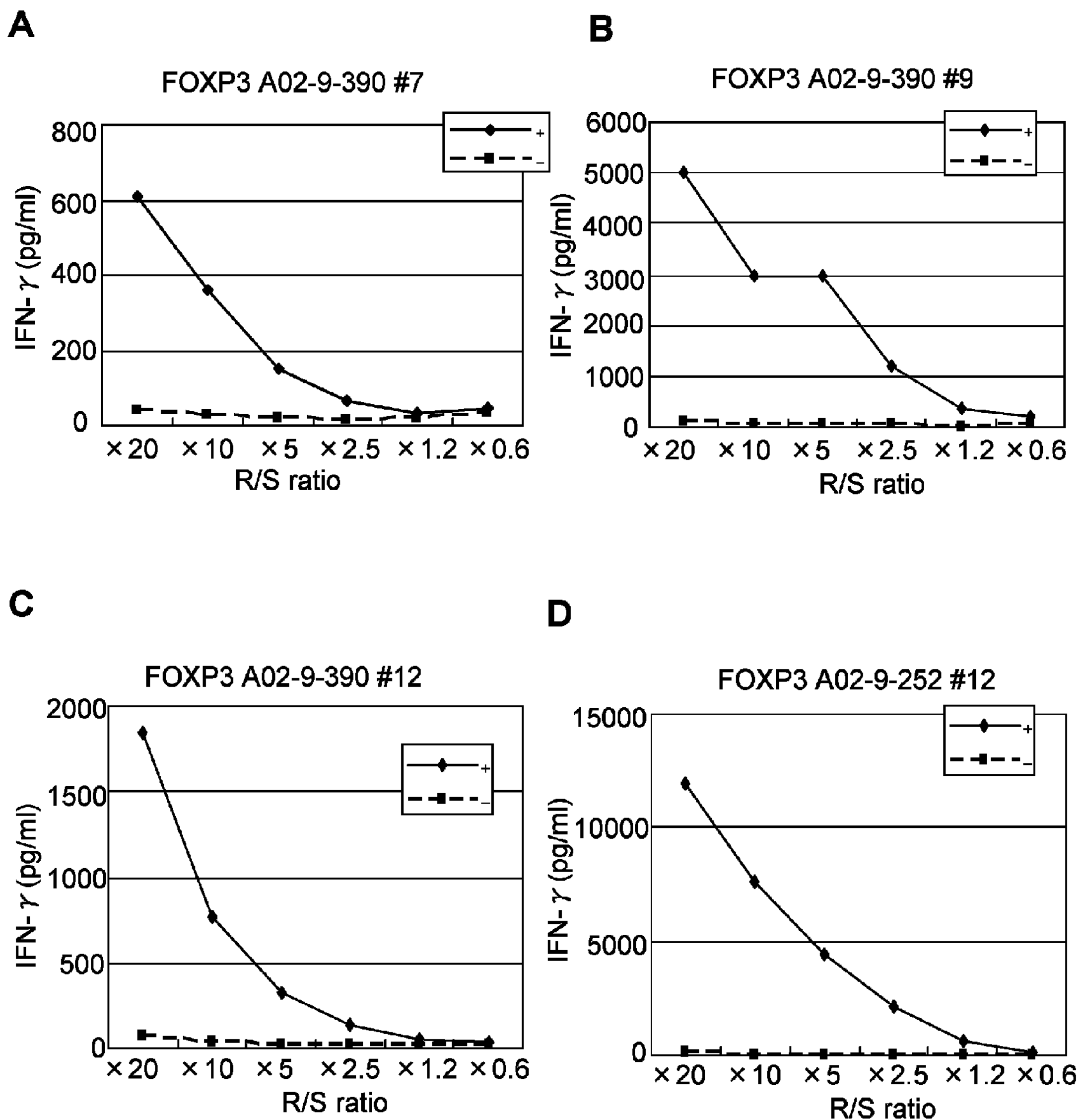

Fig. 3E-G
E
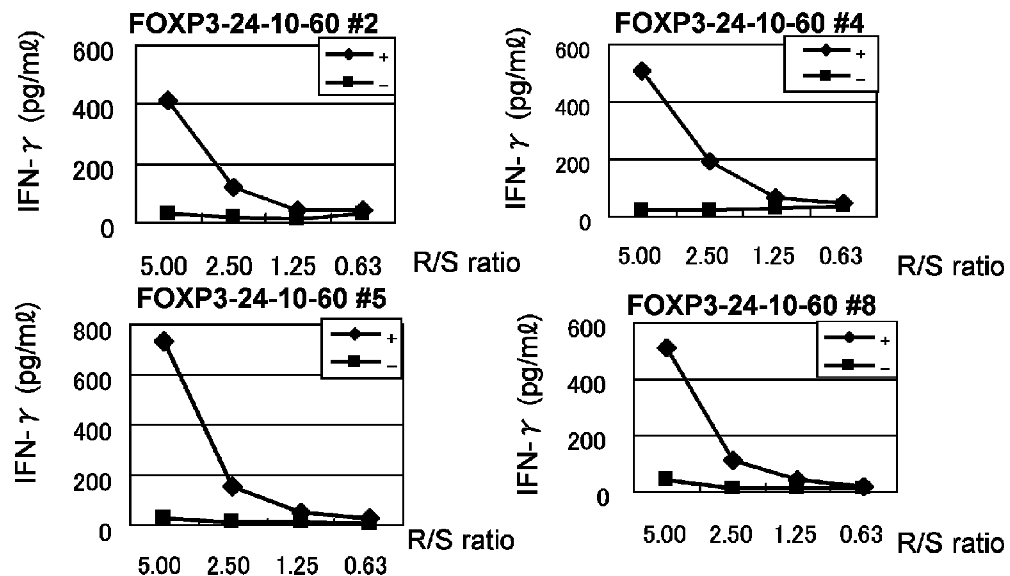
F
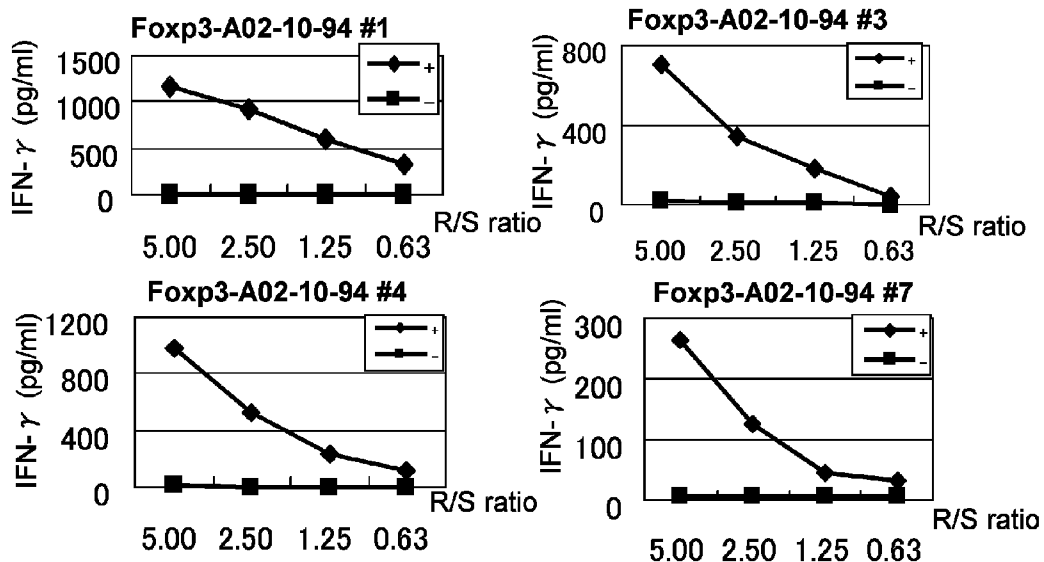
G
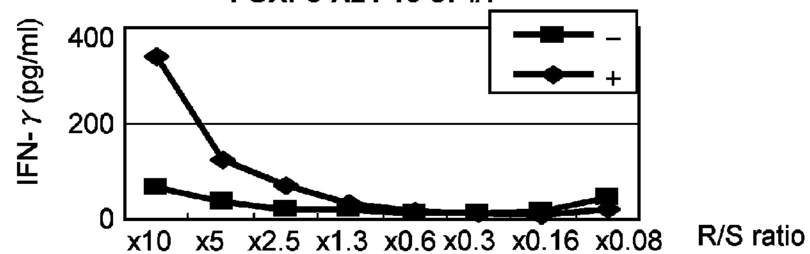

A
293T Foxp3-A02-9-390
IFN-γ (pg/ml)
0
2
4
6
8
10
7
3.5
1.7
0.8
0.4
0.2
R/S ratio
A02+Foxp3
A02/Foxp3-9-252 pep
A02+HIG2
Foxp3
B
293T Foxp3-A02-9-252
IFN-γ (pg/ml)
0
2
4
6
8
10
6.8
3.4
1.7
0.8
0.4
0.2
R/S ratio
A02+Foxp3
A02/Foxp3-9-390 pep
A02+TTK
Foxp3
C
293T Foxp3-A24-9-252
IFN-γ (pg/ml)
0
2
4
6
8
10
12
4.6
2.3
1.6
0.8
0.4
0.2
R/S ratio
A24+Foxp3
A24/Foxp3-10-341 pep
A24+INHBB
Foxp3

A
Foxp3-9-252_h
Spot forming cells
80
70
60
50
40
30
20
10
0
peptide +
peptide −
40 20 10 40 20 10 40 20 10 40 20 10 40 20 10 40 20 10 40 20 10 40 20 10
M1
M2
M3
M4
M5
N1
N2
N3
B
Foxp3-9-252_m
Spot forming cells
160
140
120
100
80
60
40
20
0
peptide +
peptide −
40 20 10 40 20 10 40 20 10 40 20 10 40 20 10 40 20 10 40 20 10 40 20 10
M1
M2
M3
M4
M5
N1
N2
N3

*, P <0.01; **, P <0.005

Fig. 7A-B
A
20
Foxp3-9-252-9V Foxp3-9-252-WT Peptide (-)
R/S ratio
4
2
1
0.5
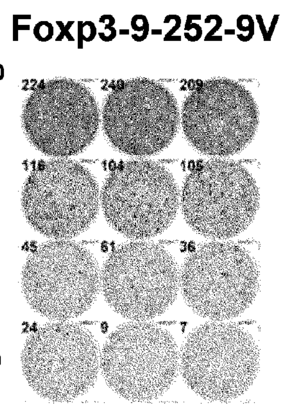
233 240 262
120 142 110
22 31 46
15 7 18
1 1 1
0 0 0
0 1 0
0 0 0
21
Responder : Foxp3-9-252-WT CTL
Stimulator : peptide-pulsed T2 cells
B
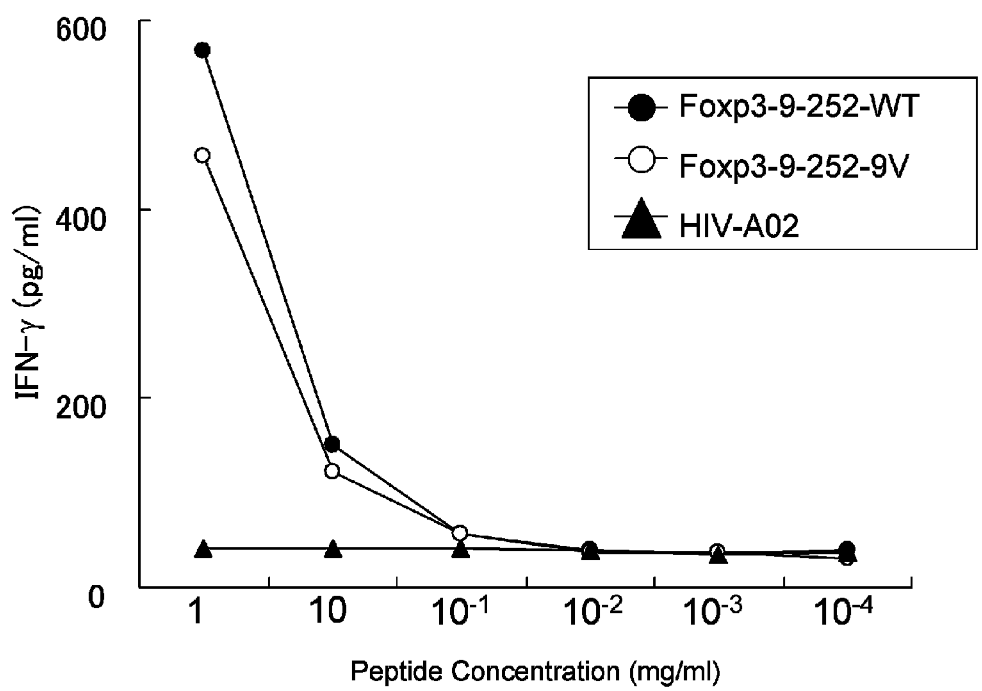

Fig. 7C-D
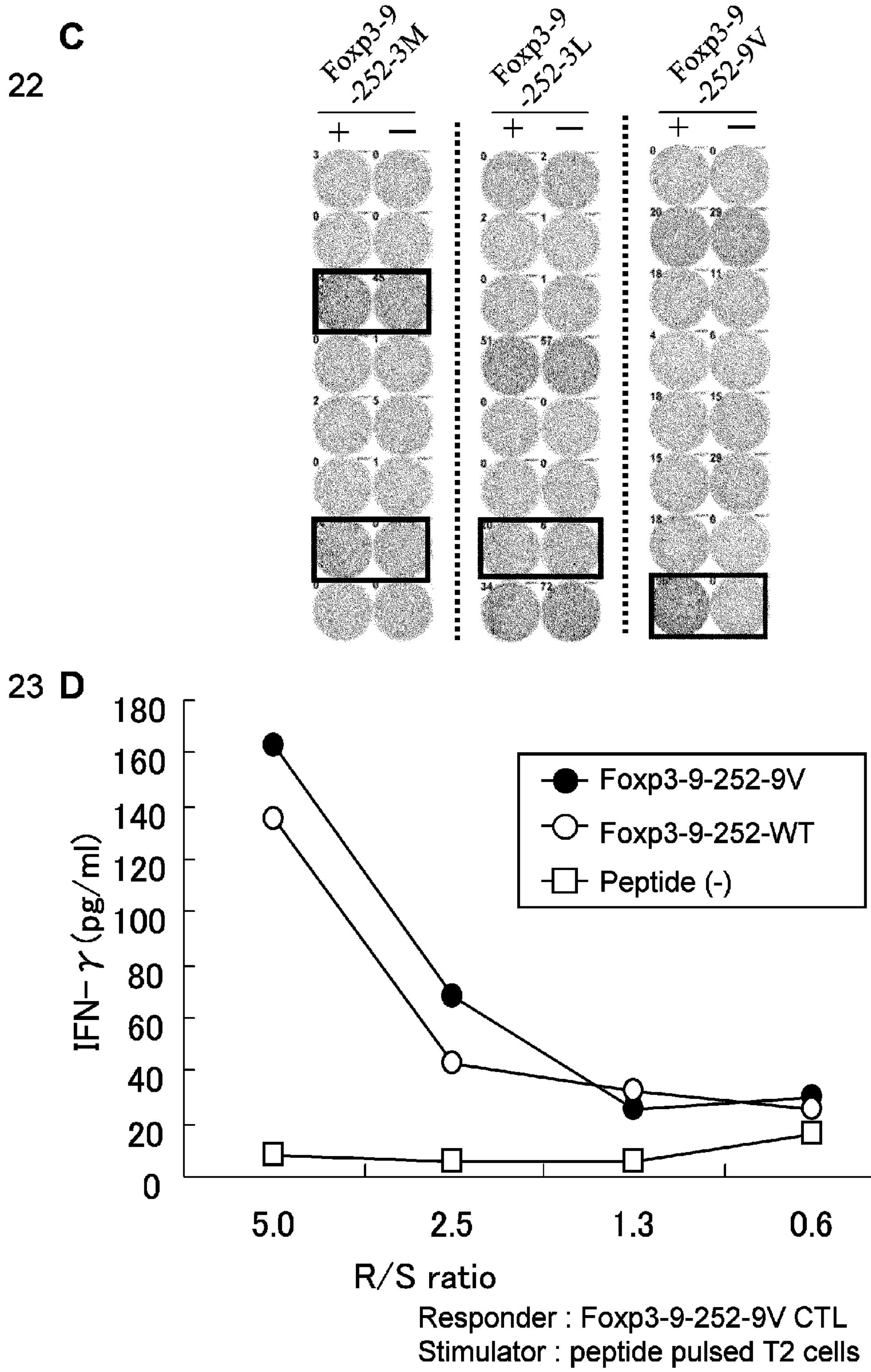

FOXP3 PEPTIDE VACCINE

CROSS-REFERENCES TO RELATED APPLICATIONS

The present application is a U.S. National Phase of PCT/JP2007/001466, filed Dec. 26, 2007, which claims the benefit of U.S. Provisional Application No. 60/878,615, filed on Jan. 3, 2007, and U.S. Provisional Application No. 60/896,472, filed on Mar. 22, 2007, the disclosures of which are hereby incorporated herein by reference in their entirety.

The present invention relates to the field of biological science, more specifically to the field of cancer therapy. In particular, the present invention relates to Foxp3 peptides that are extremely effective as cancer vaccines, and drugs for treating and preventing tumors.

BACKGROUND ART

It has been demonstrated that CD8+ cytotoxic T lymphocytes (CTLs) recognize epitope peptides derived from tumor-associated antigens (TAAs) presented on MHC class I molecule, and then kill the tumor cells. Since the discovery of the MAGE family as the first example of TAAs, many other TAAs have been discovered using immunological approaches (Boon T, Int J Cancer 54: 177-80, 1993; Boon T et al., J Exp Med 183: 725-9, 1996; van der Bruggen P et al., Science 254: 1643-7, 1991; Brichard V et al., J Exp Med 178: 489-95, 1993; Kawakami Y et al., J Exp Med 180: 347-52, 1994), and some of them have now been in the process of clinical development as targets of immunotherapy.

Identification of new TAAs, which induce potent and specific anti-tumor immune responses, warrants further development of clinical applications of peptide vaccination strategies in various types of cancer (Harris C C, J Natl Cancer Inst 88: 1442-5, 1996; Butterfield L H et al., Cancer Res 59: 3134-42, 1999; Vissers J L M et al., Cancer Res 59: 5554-9, 1999; Van der Burg S H et al., J Immunol 156: 3308-14, 1996; Tanaka F et al., Cancer Res 57: 4465-8, 1997; Fujie T et al., Int J Cancer 80: 169-72, 1999; Kikuchi M et al., Int J Cancer 81: 459-66, 1999; Oiso M et al., Int J Cancer 81: 387-94, 1999).

Various kinds of antigen specific immunotherapy have been performed, however, low clinical efficacy has been obtained so far in terms of obvious tumor regression (Rosenberg S A et al., Nat Med 10:909-15, 2004). One of the major reasons is the poor immune response of tumor-infiltrating lymphocytes (TIL) and peripheral blood lymphocytes (PBL) from patients with advanced-stage cancer (Miescher S et al., J Immunol 136: 1899-907, 1986). This immunosuppression induced by tumor is the reason for poor responses to tumor antigens (Young R C et al., Am J Med 52: 63-8, 1972), poor proliferation of T cells (Alexander J P et al., Cancer Res 53: 1380-7, 1993), loss of cytokine production (Horiguchi S et al., Cancer Res 59: 2950-6, 1999), and defective signal transduction of T cells and natural killer cells (Kono K et al., Clin Cancer Res 11: 1825-8, 1996, Kiessling R et al., Cancer Immunol Immunother 48: 353-62, 1999).

To improve the clinical efficacy for immunotherapy, it is important to overcome the effect of immunosuppressive factors induced by tumors. Immunological tolerance and protection from autoimmunity are conferred by central and peripheral mechanisms including clonal deletion of self-reactive T cells in thymus and the induction of anergy upon encounter with autoantigens in the peripherary. Recently, it has been clarified that regulatory T cells (T-regs), characterized by coexpression of CD4 and CD25 markers, are a functionally unique population of T cells and function to maintain immune homeostasis (Sakaguchi S et al., J Immunol. 155: 1151-64, 1995, Dieckmann D et al., J Exp Med 193: 1303-10, 2001). T-reg cells are one of the major players to suppress the various types of immune response (Miescher S et al., J Immunol 136: 1899-907, 1986; Young R C et al., Am J Med 52: 63-72, 1972; Alexander J P et al., Cancer Res 53: 1380-7, 1997; Horiguchi S et al., Cancer Res 59: 2950-6, 1999; Kono K et al., Clin Cancer Res 11: 1825-8, 1996; Kiessling R et al., Cancer Immunol Immunother 48: 353-62, 1999).

Although the molecular interactions and signaling pathways that are critical for generation and function of T-regs are not yet fully elucidated, T-regs require forkhead transcription factor scurfin (Foxp3; SEQ ID NO 2) encoded by the Foxp3 gene (GenBank Accession No. NM_014009; SEQ ID NO 1), which controls their development and regulatory properties (Fontenot J D et al., Nat Immunol 4: 330-6, 2003, Hori S et al., Science 299: 1057-61, 2003, Khattri R et al., Nat Immunol 4: 304-6, 2003). Further, vaccination of mice with Foxp3 mRNA-transfected dendritic cells elicited a Foxp3-specific CTL response (Smita N et al., Cancer Res. January 1; 67(1): 371-80, 2007).

Thus, Foxp3 serves as a target for cancer immunotherapy and furthermore, partial peptides of the protein encoded by Foxp3 serve as antigens recognized by CTL.

SUMMARY OF THE INVENTION

To improve the clinical efficacy for immunotherapy, it is important to overcome the immunosuppressive factors induced by tumor. T-reg has been found to be one of the major players to suppress the various types of immune response. Therefore, it is crucial to develop the vaccine targeting Foxp3 expressing T-reg to overcome T-reg-induced immunosuppression.

The present invention is based, at least in part, on the identification of epitope peptides from the gene product of Foxp3 which elicit cytotoxic T lymphocytes (CTLs) specific to the corresponding Foxp3 peptides or epitopes. Peripheral Blood Mononuclear Cells (PBMC) of healthy donor were stimulated using HLA-A*24 and HLA-A*02 binding candidate peptides from Foxp3. It was demonstrated that these peptides are HLA-A24 or HLA-A02 restricted epitope peptides that can induce potent and specific immune responses against T-regs expressing Foxp3.

Accordingly, the present invention provides methods for regulating immunosuppression, which methods comprise the step of administering Foxp3 polypeptides of the invention. Anti-immunosuppression (i.e., reversing or counteracting immunosuppression), for example, of cytotoxic T lymphocytes, is induced by the administration of the Foxp3 polypeptides. Thus, the present invention provides methods for inducing anti-immunosuppression, which methods comprise the step of administering the Foxp3 polypeptides, as well as pharmaceutical agents for regulating immunosuppression, comprising the Foxp3 polypeptides.

In one aspect, the invention provides peptides, the peptides comprising or consisting of an amino acid sequence selected from the group consisting of SEQ ID NOs: 3-5, 7-9, 12, 15-19, 22, 24, 27-30, 37, 67 or 74.

In another aspect, the invention provides peptides having cytotoxic T cell inducibility, wherein the peptide comprises or consists of the amino acid sequence selected from the group of:

(a) SEQ ID NOs: 3-5, 7-9, 12, 17, 67 or 74; and (b) SEQ ID NOs: 3-5, 7-9, 12, 17, 67 or 74, wherein 1, 2, or several amino acids are substituted or added.

In a further aspect, the invention provides peptides having cytotoxic T cell inducibility, wherein the peptide comprises the amino acid sequence selected from the group of:

(a) SEQ ID NOs: 15-19, 22, 24, 27-30, or 37, and (b) SEQ ID NOs: 15-19, 22, 24, 27-30, or 37, wherein 1, 2, or several amino acids are substituted or added.

With respect to the embodiments, in some embodiments, the second amino acid from the N-terminus is phenylalanine, tyrosine, methionine, or tryptophan. In some embodiments, the C-terminal amino acid is phenylalanine, leucine, isoleucine, tryptophan, or methionine. In some embodiments, the second amino acid from the N-terminus is leucine or methionine. In some embodiments, the C-terminal amino acid is valine or leucine. For example, the substituted peptide comprises the amino acid sequence of SEQ ID NO: 95, 97 or 98

The invention further provides compositions comprising Foxp3 peptides of the invention or polynucleotides encoding Foxp3 peptides of the invention, and a pharmaceutically acceptable carrier or excipient. In some embodiments, the compositions are formulated to be administered as a vaccine.

The compositions can comprise one peptide or a plurality of different Foxp3 peptides of the invention. The compositions are useful for inhibiting T-reg cells, for example, inhibiting the proliferation or suppressing the function of a T-reg cell.

In some embodiments, the compositions comprise one or more Foxp3 peptides that elicit an immune response that inhibits T-reg cells in a subject whose HLA antigen is HLA-A24. In some embodiments, the compositions comprise one or more Foxp3 peptides that elicit an immune response that inhibits T-reg cells in a subject whose HLA antigen is HLA-A02.

In another aspect, the invention provides compositions comprising a polynucleotide encoding a Foxp3 peptide of the invention. In some embodiments, the compositions comprise a plurality (i.e., two or more) polynucleotides encoding a plurality of Foxp3 peptides of the invention. In some embodiments, the compositions comprise a polynucleotide that encodes a plurality of Foxp3 peptides of the invention.

In some embodiments, the compositions comprise another peptide which has the ability to induce cytotoxic T cells against cancerous cells or another polynucleotide encoding the other peptide.

In a further aspect, the invention provides an exosome that presents on its surface a complex comprising an HLA antigen and a Foxp3 peptide of the invention. In some embodiments, the HLA antigen is selected from the group consisting of HLA-A24, HLA-A2402, HLA-A02 and HLA-A0201.

In a related aspect, the invention provides methods for treating cancer (e.g., reducing tumor cell growth, promoting tumor cell death) by administering to an individual a Foxp3 peptide or a polynucleotide encoding a Foxp3 peptide.

In another aspect, the invention provides methods of inducing antigen-presenting cells having high cytotoxic T cell inducibility by administering a Foxp3 peptide of the invention or a polynucleotide encoding the Foxp3 peptide.

In another aspect, the invention provides methods of inducing cytotoxic T cells by administering a Foxp3 peptide of the invention or a polynucleotide encoding the Foxp3 peptide.

In a related aspect, the invention provides an isolated cytotoxic T cell, which is induced by a Foxp3 peptide of the invention.

In another aspect, the invention provides an antigen-presenting cell, which comprises a complex formed between an HLA antigen and a Foxp3 peptide of the invention. In some embodiments, the antigen presenting cell is isolated.

In a further aspect, the invention provides methods of regulating T-reg cells in a subject comprising administering to the subject a vaccine comprising a Foxp3 peptide of the invention or an immunologically active fragment of the peptide, or a polynucleotide encoding the peptide.

In practicing the methods of treatment, the subject or patient can be a human. It is to be understood that both the foregoing summary of the invention and the following detailed description are of exemplified embodiments, and not restrictive of the invention or other alternate embodiments of the invention.

BRIEF DESCRIPTION OF THE DRAWINGS

FIG. 1 depicts photographs showing the results of IFN-gamma ELISPOT assay on CTLs that were induced with peptides derived from Foxp3. In FIG. 1A, the CTLs in well numbers #2 and 7 stimulated with Foxp3-A24-9-363 (SEQ ID NO 3), #1 and #6 with Foxp3-A24-9-366 (SEQ ID NO 7), #5 with Foxp3-A24-9-190 (SEQ ID NO 9), and #7 with Foxp3-A24-10-87 (SEQ ID NO 67), and with Foxp3-A24-10-60 (SEQ ID NO 74) showed potent IFN-gamma production compared with the control. In FIG. 1B, the CTLs in well number #4 stimulated with Foxp3-A24-9-207 (SEQ ID NO 4), #6 with Foxp3-A24-9-332 (SEQ ID NO 5), #6 with Foxp3-A24-9-337 (SEQ ID NO 8), and #1 with Foxp3-A24-10-114 (SEQ ID NO 12) showed potent IFN-gamma production compared with the control.

FIG. 2 depicts photographs showing the results of IFN-gamma ELISPOT assay on CTLs that were induced with peptides derived from Foxp3. In FIG. 2A, the CTLs in well number #2 stimulated with Foxp3-A2-9-390 (SEQ ID NO 15), #2 with Foxp3-A2-9-69 (SEQ ID NO 16), #6 with Foxp3-A2-9-252 (SEQ ID NO 17), #4 with Foxp3-A2-10-359 (SEQ ID NO 22), #7 with Foxp3-A2-263 (SEQ ID NO 24), and #2 and #5 with Foxp3-A2-10-94 (SEQ ID NO 27) showed potent IFN-gamma production compared with the control. In FIG. 2B, the CTLs in all wells stimulated with Foxp3-A2-10-233 (SEQ ID NO 28), well numbers #6 and #7 with Foxp3-A2-10-152 (SEQ ID NO 29), #5 with Foxp3-A2-10-77 (SEQ ID NO 30), and #1 with Foxp3-A2-10-246 (SEQ ID NO 37), and with Foxp3-A2-10-94 (SEQ ID NO 27) showed potent IFN-gamma production compared with the control.

In FIG. 2C, the CTLs in well numbers #1, #2, #4, #5, #7, #9, #11 and #12 with Foxp3-A2-9-390 (SEQ ID NO 15), #5 and #11 with Foxp3-A2-9-304 (SEQ ID NO 19), #7 with Foxp3-A2-9-68 (SEQ ID NO 7) and #12 with Foxp3-A2-9-252 (SEQ ID NO 17) showed potent IFN-gamma production compared with the control.

FIG. 3 shows that the cells in the positive wells were expanded and performed IFN-gamma ELISA assay. In FIGS. 3A, B and C, CTL lines stimulated with Foxp3-A02-9-390 (SEQ ID NO: 15) (solid diamond) showed potent IFN-gamma production compared with the control (solid square). In FIG. 3D, CTL lines stimulated with Foxp3-A02-9-252 (SEQ ID NO: 17) (solid diamond) showed potent IFN-gamma production compared with the control (solid square).

In FIG. 3E CTL lines stimulated with Foxp3-A24-10-60 (SEQ ID NO: 74) (solid diamond) showed potent IFN-gamma production compared with the control (solid square). In FIG. 3F CTL lines stimulated with Foxp3-A02-10-94 (SEQ ID NO: 27) (solid diamond) showed potent IFN-gamma production compared with the control (solid square). In FIG. 3G CTL lines stimulated with Foxp3-A24-10-87 (SEQ ID NO: 67) (solid diamond) showed potent IFN-gamma production compared with the control (solid square).

In FIGS. 4A and B, CTL lines raised by Foxp3-A02-9-390 (SEQ ID NO: 15) and Foxp3-A02-9-252 (SEQ ID NO: 17) showed high specific CTL activity against 293T that transfected both Foxp3 and HLA-A02. On the other hand, it did not show significant specific CTL activity against controls. In FIG. 4C, CTL lines raised by Foxp3-A02-9-252 (SEQ ID NO: 17) showed high specific CTL activity against 293T that transfected both Foxp3 and HLA-A24. On the other hand, it did not show significant specific CTL activity against controls.

FIG. 7 shows assay for affinity of Foxp3-9-252 substitutions to HLA molecule. In FIG. 7A CTLs induced with Foxp3-9-252-WT recognize the cells presenting Foxp3-9-252-9V peptide on HLA-A2 molecule. IFN-gamma ELISPOT assay was performed using CTL line induced with Foxp3-9-252-WT peptide as responder cells and T2 cells pulsed Foxp3-9-252-WT or Foxp3-9-252-9V peptide as stimulator cells, respectively. T2 cells without peptide pulse were prepared as control. In FIG. 7B Foxp3-9-252-9V and Foxp3-9-252-WT show similar affinity to HLA-A2 molecule. IFN-gamma ELISA assay was performed using CTL line induced with Foxp3-9-252-WT peptide as responder cells ($1\times10^5$ cells/well) and Foxp3-9-252-WT (-solid circle-), Foxp3-9-252-9V (-open circle-) or HIV-A02 (-solid triangle-) peptide pulsed T2 cells as stimulator cells ($1\times10^4$ cells/well). Peptide pulse of stimulator cells was conducted at 37 degree Celsius for 2 hours in each kind of peptide and peptide concentration.

In FIG. 7C CTLs could be induced by stimulation with Foxp3-9-252 substitutions targeted HLA-A2 molecule. CTLs for all substituted peptides targeted HLA-A2 molecule were generated in the way as described in "Materials and Methods". The cells in the well number 3 and 7 stimulated with Foxp3-9-252-3M, the well number 7 with Foxp3-9-252-3L and the well number 8 with Foxp3-9-252-9V showed IFN-gamma production compared with the control. In FIG. 7D CTLs generated with Foxp3-9-252-9V recognize stimulator cells coated with Foxp3-9-252-WT peptide. CTL line induced with Foxp3-9-252-9V peptide was used as responder cells. T2 cells incubated with Foxp3-9-252-9V (-solid circle-) or Foxp3-9-252-WT (-open circle-) peptide and without any peptide (-open square-) were used as stimulator cells in this assay ($1\times10^4$ cells/well).

DETAILED DESCRIPTION OF THE INVENTION

I. Definitions

Figure 4:
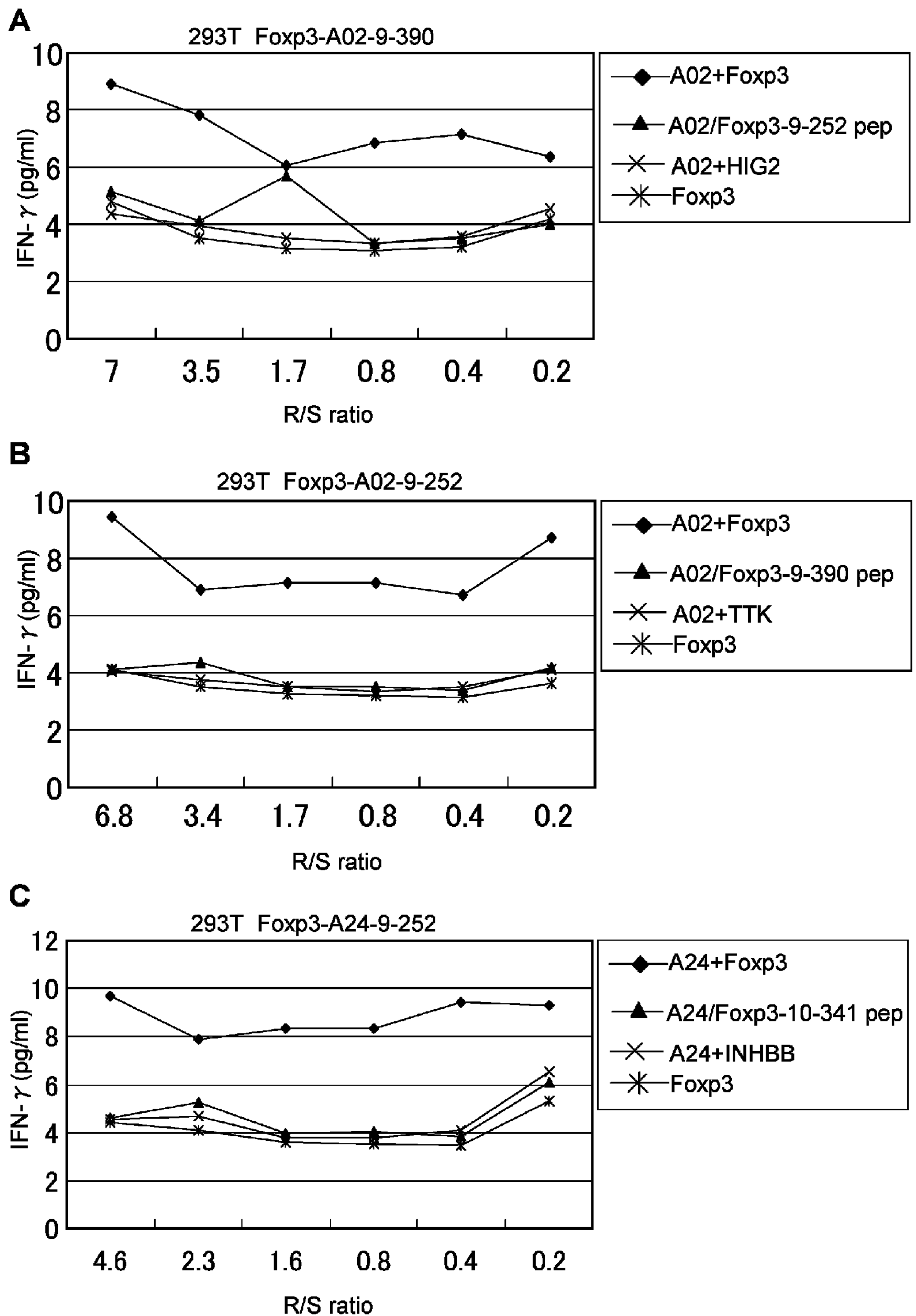
FIG. 4 shows specific CTL activity against the target cells endogenously expressing Foxp3 and HLA-A*02 or 24.

The words "a", "an", and "the" as used herein mean "at least one" unless otherwise specifically indicated.

The terms "polypeptide", "peptide" and "protein" are used interchangeably herein to refer to a polymer of amino acid residues. The terms apply to amino acid polymers in which one or more amino acid residue is a modified residue, or a non-naturally occurring residue, such as an artificial chemical mimetic of a corresponding naturally occurring amino acid, as well as to naturally occurring amino acid polymers.

The term "amino acid" as used herein refers to naturally occurring and synthetic amino acids, as well as amino acid analogs and amino acid mimetics that similarly functions to the naturally occurring amino acids. Naturally occurring amino acids are those encoded by the genetic code, as well as those modified after translation in cells (e.g., hydroxyproline, gamma-carboxyglutamate, and O-phosphoserine). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine sulfoxide, methionine methyl sulfonium). The phrase "amino acid mimetic" refers to chemical compounds that have different structures but similar functions to general amino acids.

Amino acids are referred to herein by their commonly known three letter symbols or the one-letter symbols recommended by the IUPAC-IUB Biochemical Nomenclature Commission.

The terms "gene", "polynucleotides", "nucleotides" and "nucleic acids" are used interchangeably herein unless otherwise specifically indicated and are similarly to the amino acids referred to by their commonly accepted single-letter codes.

Unless otherwise defined, all technical and scientific terms used herein have the same meaning as commonly understood by one of ordinary skill in the art to which this invention belongs. In case of conflict, the present specification, including definitions, will control.

II. Peptides

To demonstrate that peptides derived from Foxp3 function as an antigen recognized by cytotoxic T cells (CTLs), in the present invention, peptides that are subsequences of Foxp3 were analyzed whether they are antigen epitopes restricted by HLA-A24 or HLA-A02 which are common HLA alleles in the world (Date Y et al., Tissue Antigens 47: 93-101, 1996; Kondo A et al., J Immunol 155: 4307-12, 1995; Kubo R T et al., J Immunol 152: 3913-24, 1994). Candidates of HLA-A24 and HLA-A02 binding peptides that are subsequences of Foxp3 were identified using the information on their binding affinities to HLA-A24 and HLA-A02. After in vitro stimulation of T-cells by dendritic cells (DCs) loaded with these peptides, CTLs were successfully established using Foxp3-A24-9-363 (SEQ ID NO 3),
Foxp3-A24-9-366 (SEQ ID NO 7),
Foxp3-A24-9-190 (SEQ ID NO 9),
Foxp3-A24-9-207 (SEQ ID NO 4),
Foxp3-A24-9-332 (SEQ ID NO 5),
Foxp3-A24-9-337 (SEQ ID NO 8),
Foxp3-A24-10-114 (SEQ ID NO 12),
Foxp3-A2-9-390 (SEQ ID NO 15), Foxp3-A2-9-69 (SEQ ID NO 16),
Foxp3-A2-9-252 (SEQ ID NO 17),
Foxp3-A2-10-359 (SEQ ID NO 22),
Foxp3-A2-10-263 (SEQ ID NO 24),
Foxp3-A2-10-94 (SEQ ID NO 27),
Foxp3-A2-10-233 (SEQ ID NO 28),
Foxp3-A2-10-152 (SEQ ID NO 29),
Foxp3-A2-10-77 (SEQ ID NO 30),
Foxp3-A2-10-246 (SEQ ID NO 37),
Foxp3-A2-9-68 (SEQ ID NO 18),
Foxp3-A2-9-304 (SEQ ID NO 19),
Foxp3-A24-10-87 (SEQ ID NO 67) and
Foxp3-A24-10-60 (SEQ ID NO 74).

These established CTLs showed potent specific CTL activity against the peptide pulsed target cells. These results are consistent with the conclusion that Foxp3 is an antigen recognized by CTL and that
Foxp3-A24-9-363 (SEQ ID NO 3),
Foxp3-A24-9-366 (SEQ ID NO 7),
Foxp3-A24-9-190 (SEQ ID NO 9),
Foxp3-A24-9-207 (SEQ ID NO 4),
Foxp3-A24-9-332 (SEQ ID NO 5),
Foxp3-A24-9-337 (SEQ ID NO 8),
Foxp3-A24-10-114 (SEQ ID NO 12),
Foxp3-A2-9-390 (SEQ ID NO 15),
Foxp3-A2-9-69 (SEQ ID NO 16),
Foxp3-A2-9-252 (SEQ ID NO 17),
Foxp3-A2-10-359 (SEQ ID NO 22),
Foxp3-A2-10-263 (SEQ ID NO 24),
Foxp3-A2-10-94 (SEQ ID NO 27),
Foxp3-A2-10-233 (SEQ ID NO 28),
Foxp3-A2-10-152 (SEQ ID NO 29),
Foxp3-A2-10-77 (SEQ ID NO 30),
Foxp3-A2-10-246 (SEQ ID NO 37),
Foxp3-A2-9-68 (SEQ ID NO 18),
Foxp3-A2-9-304 (SEQ ID NO 19),
Foxp3-A24-10-87 (SEQ ID NO 67) and
Foxp3-A24-10-60 (SEQ ID NO 74) are epitope peptides restricted by HLA-A24 and HLA-A2. Since Foxp3 is expressed in most cancer patients and is associated with immunosuppression induced by immunosuppressive factors due to tumors, Foxp3 is a good target for immunotherapy to promote the clinical efficacy of antigen specific immunotherapy against cancer.

Thus, the present invention provides nonapeptides (peptides consisting of nine amino acid residues) and decapeptides (peptides consisting of ten amino acid residues). The Foxp3 peptides of the invention bind to an HLA molecule and induce cytotoxic activity in cytotoxic T lymphocytes (CTLs). More specifically, the invention provides peptides consisting of the amino acid sequence selected from the group of SEQ ID NOs: 3-5, 7-9, 12, 15-19, 22, 24, 27-30, 37, 67 or 74.

Generally, software programs now available on the Internet, such as those described in Parker K C. et al, J Immunol. 1994 Jan. 1; 152(1): 163-75., can be used to calculate the binding affinities between various peptides and HLA antigens in silico. Binding affinity with HLA antigens can be measured in vitro as described, for example, in Parker K C. et al, J Immunol. 1994 Jan. 1; 152(1):163-75.; Nukaya I. et al, Int J Cancer. 1999 Jan. 5; 80(1):92-7.; Kuzushima K, et al. ((2001) Blood.; 98(6):1872-81.; Journal of Immunological Methods, 1995, 185: 181-190.; Protein Science, 2000, 9: 1838-1846).

Furthermore, the Foxp3 peptides of the present invention can be flanked with additional amino acid residues so long as the Foxp3 peptide retains its CTL inducibility. Such peptides with CTL inducibility can be less than about 40 amino acids, for example, less than about 20 amino acids, for example, less than about 15 amino acids. The amino acid sequence flanking the peptides consisting of the amino acid sequence selected from the group of SEQ ID NOs: 3-5, 7-9, 12, 15-19, 22, 24, 27-30, 37, 67 and 74 is not limited and can be composed of any kind of amino acids so long as it does not inhibit the CTL inducibility of the peptide. Thus, the present invention also provides peptides having CTL inducibility, which comprises the amino acid sequence selected from the group of SEQ ID NOs: 3-5, 7-9, 12, 15-19, 22, 24, 27-30, 37, 67 and 74.

Generally, it is known that modifications of one or more amino acid in a protein do not influence the function of the protein, or in some cases even enhance the desired function of the original protein. In fact, modified peptides (i.e., peptides composed of an amino acid sequence modified by substituting or adding one, two or several amino acid residues to an original reference sequence) have been known to retain the biological activity of the original peptide (Mark et al., Proc Natl Acad Sci USA 81: 5662-6, 1984; Zoller and Smith, Nucleic Acids Res 10: 6487-500, 1982; Dalbadie-McFarland et al., Proc Natl Acad Sci USA 79: 6409-13, 1982. Thus, according to one embodiment of the invention, the peptide having CTL inducibility of the present invention can be composed of the amino acids comprising the amino acid sequence of SEQ ID NOs: 3-5, 7-9, 12, 15-19, 22, 24, 27-30, 37, 67 or 74, wherein one or more amino acids are added and/or substituted.

One of skill in the art will recognize that individual additions or substitutions to an amino acid sequence which alters a single amino acid or a small percentage of amino acids results in the conservation of the properties of the original amino acid side-chain; it is thus is referred to as "conservative substitution" or "conservative modification", wherein the alteration of a protein results in a protein with similar functions. Conservative substitution tables providing functionally similar amino acids are well known in the art. Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are conservative substitutions for one another:

1) Alanine (A), Glycine (G);
2) Aspartic acid (D), Glutamic acid (E);
3) Aspargine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

Such conservatively modified peptides are also considered to be peptides of the present invention. However, the peptide of the present invention is not restricted thereto and can include non-conservative modifications, so long as the peptide retains the CTL inducibility. Furthermore, the modified peptides do not exclude CTL inducible peptides of polymorphic variants, interspecies homologues, and alleles of Foxp3.

One can modify (add or substitute) only a small number (for example, 1, 2 or several) or a small percentage of amino acid residues while still maintaining the requisite CTL inducibility (i.e., CTL activation). Herein, the term "several" means 5 or less, or for example, 3 or less. The percentage of amino residues modified can be 20% or less, for example, 15% or 10% or less, for example, 1 to 5% of the entirety of the amino acids sequence of SEQ ID NOs: 3-5, 7-9, 12, 15-19, 22, 24, 27-30, 37, 67 and 74. Foxp3 peptides having at least 95%, 96%, 97%, 98%, 99% amino acid sequence identity to the entirety of the identified sequences are contemplated by the present invention. Sequence identity can be measured using any algorithm known in the art, for example, BLAST, available through the National Center for Biotechnology Information (on the worldwide web at ncbi.nlm.nih.gov/blast/Blast.cgi).

Homology (i.e., sequence identity) analysis of the present peptides,
Foxp3-A24-9-363 (SEQ ID NO 3),
Foxp3-A24-9-366 (SEQ ID NO 7),
Foxp3-A24-9-190 (SEQ ID NO 9),
Foxp3-A24-9-207 (SEQ ID NO 4),
Foxp3-A24-9-332 (SEQ ID NO 5),
Foxp3-A24-9-337 (SEQ ID NO 8),
Foxp3-A24-10-114 (SEQ ID NO 12),
Foxp3-A2-9-390 (SEQ ID NO 15),
Foxp3-A2-9-69 (SEQ ID NO 16),
Foxp3-A2-9-252 (SEQ ID NO 17),
Foxp3-A2-10-359 (SEQ ID NO 22),
Foxp3-A2-10-263 (SEQ ID NO 24),
Foxp3-A2-10-94 (SEQ ID NO 27),
Foxp3-A2-10-233 (SEQ ID NO 28),
Foxp3-A2-10-152 (SEQ ID NO 29),
Foxp3-A2-10-77 (SEQ ID NO 30),
Foxp3-A2-10-246 (SEQ ID NO 37),
Foxp3-A2-9-68 (SEQ ID NO 18),
Foxp3-A2-9-304 (SEQ ID NO 19),
Foxp3-A24-10-87 (SEQ ID NO 67) and
Foxp3-A24-10-60 (SEQ ID NO 74) showed that they do not have significant homology with peptides derived from any other known human gene products. This lowers the possibility of unknown or undesired immune responses when used for immunotherapy.

When used in immunotherapy, the present peptides will be presented on the surface of a cell or exosome as a complex with an HLA antigen. Therefore, peptides are selected with high binding affinity to the HLA antigen in addition to their CTL inducibility. Moreover, the peptides can be modified by substitution, addition and such of the amino acid residues to achieve a higher binding affinity. In addition to peptides that are naturally displayed, since the regularity (i.e., consistency) of the sequences of peptides displayed by binding to HLA antigens is already known (J Immunol 152: 3913, 1994; Immunogenetics 41: 178, 1995; J Immunol 155: 4307, 1994), modifications based on such regularity can be performed on the immunogenic peptides of the invention. For example, peptides showing high HLA-A24 binding affinity can have their second amino acid from the N-terminus substituted with phenylalanine, tyrosine, methionine, or tryptophan, and peptides whose amino acid at the C-terminus is substituted with phenylalanine, leucine, isoleucine, tryptophan, or methionine also find use. On the other hand, peptides which second amino acid from the N-terminus is substituted with leucine or methionine, and in which the C-terminal amino acid is substituted with valine or leucine can be used as peptides with high HLA-A02 binding affinity. The substitution is performed not only at the terminus amino acids but also at the position of potential TCR recognition of peptides. Zaremba et al. demonstrated that amino acid substitutions in CAP1 peptide can be equal to or better than the original (Cancer Res. 57, 4570-4577, 1997). For example, the substituted peptide comprises the amino acid sequence of SEQ ID NO: 95, 97 or 98. Furthermore, one to two amino acids can also be added to the N and/or C-terminus of the peptides. Such modified peptides with high HLA antigen binding affinity are also included in the present invention.

However, when the peptide sequence is identical to a portion of the amino acid sequence of an endogenous or exogenous protein having a different function, side effects such as autoimmune disorders or allergic symptoms against specific substances may be induced. Therefore, homology searches can be performed using available databases to avoid, reduce or minimize situations in which the sequence of the peptide matches the amino acid sequence of another protein. When it becomes clear from the homology searches that there exists no other peptide with 1 or 2 amino acids difference to the objective peptide, the objective peptide can be modified in order to increase the binding affinity with HLA antigens, and/or increase the CTL inducibility without any danger of the side effects.

Peptides having high binding affinity to the HLA antigens as described above will be highly effective. The candidate peptides, which are selected according to the presence of high binding affinity as an indicator, can also be examined for the actual presence of CTL inducibility. Herein, the phrase "CTL inducibility" indicates the ability of the peptide to induce CTLs when presented on antigen-presenting cells. Further, "CTL inducibility" includes the ability of the peptide to induce CTL activation, CTL proliferation, and to increase IFN-gamma production.

Confirmation of CTL inducibility can be accomplished by inducing antigen-presenting cells carrying human MHC antigens (for example, B-lymphocytes, macrophages, and dendritic cells), or more specifically dendritic cells derived from human peripheral blood mononuclear leukocytes, and after stimulation with the peptides, mixing with CD8-positive cells, and then measuring the IFN-gamma produced and released by CTL against the target cells. As the reaction system, transgenic animals that have been produced to express a human HLA antigen (for example, those described in BenMohamed L, Krishnan R, Longmate J, Auge C, Low L, Primus J, Diamond D J, Hum Immunol 61(8): 764-79, 2000 August, Related Articles, Books, Linkout Induction of CTL response by a minimal epitope vaccine in HLA A*0201/DR1 transgenic mice: dependence on HLA class II restricted T(H) response) can be used. For example, the target cells can be radiolabeled with $^{51}$Cr and such, and cytotoxic activity can be calculated from radioactivity released from the target cells. Alternatively, it can be examined by measuring IFN-gamma produced and released by CTL in the presence of antigen-presenting cells that carry immobilized peptides, and visualizing the inhibition zone on the media using anti-IFN-gamma monoclonal antibodies.

As a result of examining the CTL inducibility of the peptides as described above, those having high binding affinity to an HLA antigen did not necessarily have high inducibility. Furthermore, nonapeptides or decapeptides selected from peptides comprising the amino acid sequences indicated by SEQ ID NOs: 3-5, 7-9, 12, 15-19, 22, 24, 27-30, 37, 67 or 74, showed particularly high CTL inducibility as well as high binding affinity to an HLA antigen.

In addition to the above-mentioned modification of the present peptides, the peptides of the present invention can be further linked to other substances, so long as they retain the CTL inducibility. Usable substances include: peptides, lipids, sugar and sugar chains, acetyl groups, natural and synthetic polymers, etc. The peptides can contain modifications such as glycosylation, side chain oxidation, or phosphorylation; so long as the modifications do not destroy the biological activity of the peptides as described herein. These kinds of modifications can be performed to confer additional functions (e.g., targeting function, and delivery function) or to stabilize the polypeptide.

For example, to increase the in vivo stability of a polypeptide, it is known in the art to introduce particularly useful various D-amino acids, amino acid mimetics or unnatural amino acids; this concept can also be adopted for the present polypeptides. The stability of a polypeptide can be assayed in a number of ways. For instance, peptidases and various biological media, such as human plasma and serum, have been used to test stability (see, e.g., Verhoef et al., Eur J Drug Metab Pharmacokin 11: 291-302, 1986).

III. Preparation of the Peptides

The peptides of the invention can be prepared using well known techniques. For example, the peptides can be prepared synthetically, by recombinant DNA technology or chemical synthesis. Peptides of the invention can be synthesized individually or as longer polypeptides comprising two or more peptides (e.g., two or more Foxp3 peptides or a Foxp3 peptide and a non-Foxp3 peptide). The peptides can be isolated i.e., purified to be substantially free of other naturally occurring host cell proteins and fragments thereof, e.g., at least about 70%, 80% or 90% purified.

A peptide of the present invention can be obtained through chemical synthesis based on the selected amino acid sequence. For example, conventional peptide synthesis methods that can be adopted for the synthesis includes:

(i) Peptide Synthesis, Interscience, New York, 1966;
(ii) The Proteins, Vol. 2, Academic Press, New York, 1976;
(iii) Peptide Synthesis (in Japanese), Maruzen Co., 1975;
(iv) Basics and Experiment of Peptide Synthesis (in Japanese), Maruzen Co., 1985;
(v) Development of Pharmaceuticals (second volume) (in Japanese), Vol. 14 (peptide synthesis), Hirokawa, 1991;
(vi) WO99/67288; and
(vii) Barany G. & Merrifield R. B., Peptides Vol. 2, "Solid Phase Peptide Synthesis", Academic Press, New York, 1980, 100-118.

Alternatively, the present peptides can be obtained adopting any known genetic engineering methods for producing peptides (e.g., Morrison J. (1977) J. Bacteriology 132: 349-51; Clark-Curtiss & Curtiss (1983) Methods in Enzymology (eds. Wu et al.) 101: 347-62). For example, first, a suitable vector harboring a polynucleotide encoding the objective peptide in an expressible form (e.g., downstream of a regulatory sequence corresponding to a promoter sequence) is prepared and transformed into a suitable host cell. The host cell is then cultured to produce the peptide of interest. The peptides can also be produced in vitro adopting an in vitro translation system.

IV. Polynucleotides

The present invention provides polynucleotides which encode any of the aforementioned peptides of the present invention. These include polynucleotides derived from the natural occurring Foxp3 gene and those having a conservatively modified nucleotide sequence thereof. Herein, the phrase "conservatively modified nucleotide sequence" refers to sequences which encode identical or essentially identical amino acid sequences. Because of the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a peptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C, and G, T is replaced by U in an RNA.

The Foxp3 polynucleotides of the present invention can encode multiple Foxp3 peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotides can include any additional sequences to the coding sequence encoding the peptide of the present invention. For example, the polynucleotides can be recombinant polynucleotides that include regulatory sequences required for the expression of the peptide. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, the polynucleotides can be produced by insertion into an appropriate vector, which can be expressed when transfected into a competent cell. Alternatively, the polynucleotides can be amplified using PCR techniques or expression in suitable hosts (see, e.g., Sambrook et al., Molecular Cloning: A Laboratory Manual, Cold Spring Harbor Laboratory, New York, 1989). Alternatively, the polynucleotides can be synthesized using the solid phase techniques, as described in Beaucage S. L. & Iyer R. P., Tetrahedron 48: 2223-311, 1992; Matthes et al., EMBO J 3: 801-5, 1984.

V. Pharmaceutical Agents

Since Foxp3 has been identified as a molecule of regulatory T (T-reg) cell which cells function to maintain immune homeostasis, the Foxp3 peptides or polynucleotides encoding the Foxp3 peptides of this invention can be used for regulating T-reg cells. Thus, the present invention provides a pharmaceutical agent for regulating T-reg cells, which comprise one or more of peptides of this invention, or polynucleotides encoding the peptides as an active ingredient.

Herein, "regulating" T-reg cells indicates to modify the state of the T-reg cells in vivo, for example, by inhibiting proliferation of or suppressing the function of the T-reg cells. T-reg cell is thought to be one of the major players to suppress various types of immune response and "suppressing the function of the T-reg cells" herein means to decrease the ability of the T-reg cells to suppress an immune response. Especially, T-reg cells act in the periphery as called peripheral tolerance (Miescher S et al., J Immunol 136: 1899-907, 1986; Young R C et al., Am J Med 52: 63-72, 1972; Alexander J P et al., Cancer Res 53: 1380-7, 1997; Horiguchi S et al., Cancer Res 59: 2950-6, 1999; Kono K et al., Clin Cancer Res 11: 1825-8, 1996; Kiessling R et al., Cancer Immunol Immunother 48: 353-62, 1999; Fontenot J D et al., Nat Immunol 4: 330-6, 2003, Hori S et al., Science 299: 1057-61, 2003; Khattri R et al., Nat Immunol 4: 304-6, 2003). T-reg cells provide immunosuppressive effect, for example, in a cancer patient. Therefore, the Foxp3 peptides of the present invention, which are overexpressed in the T-reg cells, or polynucleotides encoding the Foxp3 peptides can be used as a pharmaceutical agent (e.g., vaccine) for treating cancer.

In the present invention, the phrase "vaccine" (also referred to as an immunogenic composition) refers to a substance that has the function to induce anti-tumor immunity or immunity to regulate T-regs upon inoculation into animals.

The pharmaceutical agents of the present invention can be used to treat and/or prevent cancers in subjects such as human and any other mammal including, but not limited to, mouse, rat, guinea-pig, rabbit, cat, dog, sheep, goat, pig, cattle, horse, monkey, baboon, and chimpanzee, particularly a commercially important animal or a domesticated animal.

According to the present invention, polypeptides comprising the amino acid sequence of SEQ ID NOs: 3-5, 7-9, 12, 15-19, 22, 24, 27-30, 37, 67 or 74 are HLA-A24 or HLA-A02 restricted epitope peptides that can induce potent and specific immune response against T-reg cells expressing Foxp3. Therefore, the present pharmaceutical agents are intended for the administration to subjects whose HLA antigen is either HLA-A24 or HLA-A02.

Cancers to be treated by the pharmaceutical agents of the present invention are not limited and include all kinds of cancers wherein Foxp3 is expressed in the subject. Exemplified cancers include breast cancer, AML, bladder cancer, cervical, cholangiocellular carcinoma, CML, colon and rectum, endometriosis, esophagus, gastric, gastric diffuse-type, liver, lung, lymphoma, neuroblastoma, osteosarcoma, ovarian, pancreatic cancer, prostate, renal carcinoma, small cell lung cancer, soft tissue tumor and testicular tumor.

If needed, the pharmaceutical agents of the present invention, composed of either a Foxp3 peptide or a polynucleotide encoding a Foxp3 peptide, can optionally include other therapeutic substances as an active ingredient, so long as the substance does not inhibit the T-reg cell regulating effect of the peptide of interest. For example, formulations can include anti-inflammatory agents, pain killers, chemotherapeutics, and the like. In addition to including other therapeutic substances in the medicament itself, the medicaments of the present invention can also be administered sequentially or concurrently with the one or more other pharmacologic agents. The amounts of medicament and pharmacologic agent depend, for example, on what type of pharmacologic agent(s) is/are used, the disease being treated, and the scheduling and routes of administration.

It should be understood that in addition to the ingredients particularly mentioned herein, the pharmaceutical agents of this invention can include other agents conventional in the art having regard to the type of formulation in question.

In one embodiment of the present invention, the present pharmaceutical agents can be included in articles of manufacture and kits containing materials useful for treating the pathological conditions of the disease to be treated, e.g. cancer. The article of manufacture can include a container of any of the present pharmaceutical agents with a label. Suitable containers include bottles, vials, and test tubes. The containers can be formed from a variety of materials, such as glass or plastic. The label on the container should indicate the agent is used for treating or preventing one or more conditions of the disease. The label can also indicate directions for administration and so on.

In addition to the container described above, a kit including a pharmaceutical agent of the present invention can optionally further include a second container housing a pharmaceutically-acceptable diluent. It can further include other materials desirable from a commercial and user standpoint, including other buffers, diluents, filters, needles, syringes, and package inserts with instructions for use.

The pharmaceutical compositions can, if desired, be presented in a pack or dispenser device which can contain one or more unit dosage forms containing the active ingredient. The pack can, for example, include metal or plastic foil, such as a blister pack. The pack or dispenser device can be accompanied by instructions for administration.

(1) Pharmaceutical Agents Containing the Peptides as the Active Ingredient

The peptides of this invention can be administered directly as a pharmaceutical agent, if necessary, that has been formulated by conventional formulation methods. In such cases, in addition to the peptides of this invention, carriers, excipients, and such that are ordinarily used for drugs can be included as appropriate without particular limitations. Examples of such carriers are sterilized water, physiological saline, phosphate buffer, culture fluid and such. Furthermore, the pharmaceutical agents can contain as necessary, stabilizers, suspensions, preservatives, surfactants and such. The pharmaceutical agents of this invention can be used for treating and/or preventing cancer, especially regulating T-reg cells.

The peptides of this invention can be prepared in a combination, which comprises two or more of Foxp3 peptides of the invention, to induce CTL in vivo. The Foxp3 peptides can be in a cocktail or can be conjugated to each other using standard techniques. For example, the Foxp3 peptides can be expressed as a single polypeptide sequence. The peptides in the combination can be the same or different. By administering the Foxp3 peptides of this invention, the peptides are presented at a high density on the HLA antigens of antigen-presenting cells, then CTL that specifically react toward the complex formed between the displayed peptide and the HLA antigen are induced. Alternatively, antigen presenting cells that have immobilized the Foxp3 peptides of this invention on their cell surface are obtained by removing dendritic cells from the subjects, which are stimulated by the peptides of this invention, CTL is induced in the subjects by readministering the Foxp3 peptide-loaded dendritic cells to the subjects, and as a result, aggressiveness towards the target cells can be increased.

The pharmaceutical agents for regulation of T-reg cells, which comprise a Foxp3 peptide of this invention as the active ingredient, optionally can comprise an adjuvant so that cellular immunity will be established effectively, or they can be administered with other active ingredients, and they can be administered by formulation into granules. An adjuvant refers to a compound that enhances the immune response against the protein when administered together (or successively) with the protein having immunological activity. An adjuvant that can be applied includes those described in the literature (Clin Microbiol Rev 7: 277-89, 1994). Exemplary adjuvants include aluminum phosphate, aluminum hydroxide, alum, cholera toxin, *salmonella* toxin, and such, but are not limited thereto.

Furthermore, liposome formulations, granular formulations in which the Foxp3 peptide is bound to few-mcm diameter beads, and formulations in which a lipid is bound to the peptide can be conveniently used.

In some embodiments the pharmaceutical agents of the invention comprise a component which primes cytotoxic T lymphocytes. Lipids have been identified as agents capable of priming CTL in vivo against viral antigens. For example, palmitic acid residues can be attached to the epsilon- and alpha-amino groups of a lysine residue and then linked to a peptide of the invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinlyseryl-serine (P3CSS) can be used to prime CTL when covalently attached to an appropriate peptide (see, e.g., Deres et al., Nature 342: 561, 1989).

The method of administration can be oral, intradermal, subcutaneous, intravenous injection, or such, and systemic administration or local administration to the vicinity of the targeted sites finds use. The administration can be performed by single administration or boosted by multiple administrations. The dose of the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once every a few days to once every few months. One skilled in the art can appropriately select the suitable dose.

(2) Pharmaceutical Agents Containing Polynucleotides as the Active Ingredient

The pharmaceutical agents of the invention can also comprise nucleic acids encoding the Foxp3 peptides disclosed herein in an expressible form. Herein, the phrase "in an expressible form" means that the polynucleotide, when introduced into a cell, will be expressed in vivo as a polypeptide that has induces anti-tumor immunity. In one embodiment, the nucleic acid sequence of the polynucleotide of interest includes regulatory elements necessary for expression of the polynucleotide in a target cell. The polynucleotide(s) can be equipped to stably insert into the genome of the target cell (see, e.g., Thomas K R & Capecchi M R, Cell 51: 503-12, 1987 for a description of homologous recombination cassette vectors). See, e.g., Wolff et al., Science 247: 1465-8, 1990; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922, 687).

The peptides of the invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 351: 456-60, 1991. A wide variety of other vectors useful for therapeutic administration or immunization e.g., adeno and adeno-associated virus vectors, retroviral vectors, *Salmonella typhi* vectors, detoxified anthrax toxin vectors, and the like, will be apparent. See, e.g., Shata et al., Mol Med Today 6: 66-71, 2000; Shedlock et al. J Leukoc Biol 68: 793-806, 2000; Hipp et al., In Vivo 14: 571-85, 2000.

Delivery of a polynucleotide into a patient can be either direct, in which case the patient is directly exposed to a polynucleotide-carrying vector, or indirect, in which case, cells are first transformed with the polynucleotide of interest in vitro, then transplanted into the patient. Theses two approaches are known, respectively, as in vivo or ex vivo gene therapy.

For general reviews of the methods of gene therapy, see Goldspiel et al., Clinical Pharmacy 12: 488-505, 1993; Wu and Wu, Biotherapy 3: 87-95, 1991; Tolstoshev, Ann Rev Pharmacol Toxicol 33: 573-96, 1993; Mulligan, Science 260: 926-32, 1993; Morgan & Anderson, Ann Rev Biochem 62: 191-217, 1993; Trends in Biotechnology 11(5): 155-215, 1993). Methods commonly known in the art of recombinant DNA technology which can be used are described in eds. Ausubel et al., Current Protocols in Molecular Biology, John Wiley & Sons, NY, 1993; and Krieger, Gene Transfer and Expression, A Laboratory Manual, Stockton Press, NY, 1990.

The method of administration can be oral, intradermal, subcutaneous, intravenous injection, or such, and systemic administration or local administration to the vicinity of the targeted sites finds use. The administration can be performed by single administration or boosted by multiple administrations. The dose of the polynucleotide in the suitable carrier or cells transformed with the polynucleotide encoding the peptides of this invention can be adjusted appropriately according to the disease to be treated, age of the patient, weight, method of administration, and such, and is ordinarily 0.001 mg to 1000 mg, for example, 0.001 mg to 1000 mg, for example, 0.1 mg to 10 mg, and can be administered once every a few days to once every few months. One skilled in the art can appropriately select the suitable dose.

(3) Exosomes

Alternatively, the present invention provides intracellular vesicles called exosomes, which present complexes formed between the peptides of this invention and HLA antigens on their surface. Exosomes can be prepared, for example by using the methods described in detail in Published Japanese Translation of International Publication Nos. Hei 11-510507 and 2000-512161, and can be prepared using antigen presenting cells obtained from subjects who are targets of treatment and/or prevention. The exosomes of this invention can be inoculated as vaccines, similarly to the peptides of this invention.

The type of HLA antigens used must match that of the subject requiring treatment and/or prevention. For example, for Japanese, HLA-A24, particularly HLA-A2402 is often appropriate.

Regarding HLA antigens, the use of A-24 or A-02 type that are highly expressed among the Japanese and Caucasian is favorable for obtaining effective results, and the use of subtypes including A-2402 and A-0201 find use. Typically, in the clinic, the type of HLA antigen of the patient requiring treatment is investigated in advance, which enables appropriate selection of peptides having high levels of binding affinity to this antigen, or having cytotoxic T cell (CTL) inducibility by antigen presentation. Furthermore, in order to obtain peptides showing high binding affinity and CTL inducibility, substitution or addition of 1, 2, or several amino acids can be performed based on the amino acid sequence of the naturally occurring Foxp3 partial peptide.

(4) Antigen-Presenting Cells

The present invention also provides antigen-presenting cells (APCs) that present complexes formed between HLA antigens and the peptides of this invention on its surface. The APCs that are obtained by contacting the peptides of this invention, or the nucleotides encoding the peptides of this invention can be prepared from subjects who are the targets of treatment and/or prevention, and can be administered as vaccines by themselves or in combination with other drugs including the peptides of this invention, exosomes, or cytotoxic T cells.

The APCs are not limited to any kind of cells and includes dendritic cells (DCs), Langerhans cells, macrophages, B cells, and activated T cells, all of which are known to present proteinaceous antigens on their cell surface so as to be recognized by lymphocytes. Since DC is a representative APC having the strongest CTL inducing action among APCs, DCs find particular use as the APCs of the present invention.

For example, an APC can be obtained by inducing dendritic cells from the peripheral blood monocytes and then contacting (stimulating) them with the peptides of this invention in vitro, ex vivo or in vivo. When the peptides of this invention are administered to the subjects, APCs that have the peptides of this invention immobilized to them are induced in the body of the subject. "inducing APC" includes contacting (stimulating) a cell with the peptides of this invention, or nucleotides encoding the peptides of this invention to present complexes formed between HLA antigens and the peptides of this invention on cell's surface. Alternatively, after immobilizing the peptides of this invention to the APCs, the APCs can be administered to the subject as a vaccine. For example, the ex vivo administration can comprise steps of:

a: collecting APCs from subject:, and b: contacting with the APCs of step a, with the peptide.

The APCs obtained by step b can be administered to the subject as a vaccine.

According to an aspect of the present invention, the APCs have a high level of CTL inducibility. Such APCs having a high level of cytotoxic T cell inducibility can be prepared by a method which comprises the step of transferring genes comprising polynucleotides that encode the peptides of this invention to APCs in vitro. The introduced genes can be in the form of DNAs or RNAs. For the method of introduction, without particular limitations, various methods conventionally performed in this field, such as lipofection, electroporation, and calcium phosphate method can be used. More specifically, it can be performed as described in Cancer Res 56: 5672-7, 1996; J Immunol 161: 5607-13, 1998; J Exp Med 184: 465-72, 1996; Published Japanese Translation of International Publication No. 2000-509281. By transferring the gene into APCs, the gene undergoes transcription, translation, and such in the cell, and then the obtained protein is processed by MHC Class I or Class II, and proceeds through a presentation pathway to present partial peptides.

(5) Cytotoxic T Cells

A cytotoxic T cell induced against any of the Foxp3 peptides of the present invention are supposed to strengthen the immune system targeting the T-reg cells in vivo and thus can be used as vaccines similar to the peptides. Thus, the present invention provides isolated cytotoxic T cells that are induced by any of the present peptides.

Such cytotoxic T cells can be obtained by (1) administering to a subject or (2) contacting (stimulating) subject-derived APCs, and CD8-positive cells, or peripheral blood mononuclear leukocytes in vitro with the peptide of the present invention.

The cytotoxic T cells, which have been induced by stimulation from APCs that present the peptides of this invention, can be derived from subjects who are targets of treatment and/or prevention, and can be administered by themselves or in combination with other drugs including the peptides of this invention or exosomes for the purpose of regulating effects.

The obtained cytotoxic T cells act specifically against target cells presenting the peptides of this invention, for example, the same peptides used for induction. The target cells can be cells that express Foxp3 endogenously, or cells that are transfected with Foxp3 genes, and cells that present the peptides of this invention on the cell surface due to stimulation by these peptides can also become targets of attack.

(6) TCRs

The present invention also provides a composition comprising nucleic acids encoding polypeptides that are capable of forming a subunit of a T cell receptor (TCR), and methods of using the same. The TCR subunits have the ability to form TCRs that confer specificity to T cells for cells presenting the peptide of this invention. By using the known method in the art, the nucleic acids of alpha- and beta-chain as the TCR subunits of the CTL induced with one or more peptides of this invention may be identified (WO2007/032255 and Morgan et al., J Immunol, 171, 3288 (2003)). The derivative TCRs preferably bind target cells displaying the Foxp3 peptide with high avidity, and optionally mediate efficient killing of target cells presenting the Foxp3 peptide in vivo and in vitro.

The nucleic acids encoding the TCR subunits can be incorporated into suitable vectors e.g. retroviral vectors. These vectors are well known in the art. The nucleic acids or the vectors comprising them usefully can be transferred into a T cell, which T cell is preferably from a patient. Advantageously, the invention provides an off-the-shelf composition allowing rapid modification of a patient's own T cells (or those of another mammal) to rapidly and easily produce modified T cells having excellent T-reg cell killing properties.

Also, the present invention provides CTLs which are prepared by transduction with the nucleic acids encoding the TCR subunits polypeptides binding with Foxp3 peptide of this invention. The transduced CTLs are capable of forming to T-reg cells in vivo, and expanded by well known culturing method in vitro (e.g., Kawakami et al., J Immunol., 142, 3452-3461 (1989)). The T cells of the invention can be used to form an immunogenic composition useful in treating or preventing cancer in a patient in need of therapy or protection (WO2006/031221).

VI. Methods of Using the Foxp3 Peptides

The Foxp3 peptides of the present invention and polynucleotide encoding the Foxp3 peptides can be used for inducing APCs and CTLs. The Foxp3 peptides and polynucleotides can be used in combination with any other compounds so long as the compounds do not inhibit their CTL inducibility. Thus, any of the aforementioned pharmaceutical agents of the present invention can be used for the present methods mentioned below.

(1) Methods of Inducing Antigen-Presenting Cells (APCs)

Thus, the present invention provides methods of inducing APCs using the peptides of this invention or polynucleotides encoding the peptides. The induction of APCs can be performed as described above under the item of "V-(4) Antigen-presenting cells". This invention also provides a method for inducing APCs having a high level of cytotoxic T cell inducibility, the induction of which is discussed under the item of "V-(4) Antigen-presenting cells", supra. Alternatively, according to the present invention, use of Foxp3 peptides selected from peptides comprising the amino acid sequence of SEQ ID NOs: 3-5, 7-9, 12, 15-19, 22, 24, 27-30, 37, 67 or 74, or polynulceotides encoding the Foxp3 peptides for manufacturing a pharmaceutical composition including antigen-presenting cells. Further, the present invention also provides Foxp3 peptides selected from peptides comprising the amino acid sequence of SEQ ID NOs: 3-5, 7-9, 12, 15-19, 22, 24, 27-30, 37, 67 or 74 or polynulceotides encoding the Foxp3 peptides for inducing antigen-presenting cells.

(2) Methods of Inducing Cytotoxic T Cells

Furthermore, the present invention provides methods for inducing CTLs using the Foxp3 peptides of this invention or polynulceotides encoding the Foxp3 peptides. When the Foxp3 peptides of this invention are administered to a subject, CTL is induced in the body of the subject, and the strength of the immune system targeting the T-reg cells is enhanced. Alternatively, they can be used for an ex vivo therapeutic method, in which subject-derived APCs, and CD8-positive cells, or peripheral blood mononuclear leukocytes are contacted (stimulated) with the peptides of this invention in vitro, and after inducing CTL, the cells are returned to the subject. For example, the method can comprise steps of:

a: collecting APCs from subject:, b: contacting with the APCs of step a, with the peptide:, c: mixing the APCs of step b with CD8+ T cells, and co-culturing for inducing cytotoxic T-cells:, and d: collecting CD8+ T cells from the co-culture of step c.

The CD8+ T cells having cytotoxic activity obtained by step d can be administered to the subject as a vaccine. The APCs to be mixed with the CD8+ T cells in above step c can also be prepared by transferring genes coding for the present peptides into the APCs as detailed above under the item of "V-(4) Antigen-presenting cells"; but are not limited thereto and any APC or exosome which effectively presents the present peptides to the T cells can be used for the present method. Alternatively, according to the present invention, use of Foxp3 peptides selected from peptides comprising the amino acid sequence of SEQ ID NOs: 3-5, 7-9, 12, 15-19, 22, 24, 27-30, 37, 67 or 74, or polynulceotides encoding the Foxp3 peptides for manufacturing a pharmaceutical composition including CTL. Further, the present invention also provides the Foxp3 peptides selected from peptides comprising the amino acid sequence of SEQ ID NOs: 3-5, 7-9, 12, 15-19, 22, 24, 27-30, 37, 67 or 74, or polynulceotides encoding the Foxp3 peptides for inducing CTL.

(3) Regulating Immunosuppression

As discussed above, the peptides, polynucleotides, exosomes, APCs and CTLs of the present invention can be used as vaccines to regulate (i.e., suppress) T-reg cells. Since T-reg is considered to be one of the major players to suppress various types of immune responses, particularly CTL cytotoxic activity, the ability of the peptides, polynucleotides, exosomes, APCs and CTLs of the present invention indicates that they also can be used for counteracting immunosuppression, particularly of CTL cytotoxic activity. Accordingly, the present invention provides a method of regulating T-reg cells as well as a method of regulating (i.e., counteracting) immunosuppression, the methods comprising the steps of administering the peptides, polynucleotides, exosomes, APCs or CTLs of the present invention to a subject in need thereof. Furthermore, the present invention also provides use of Foxp3 peptides selected from peptides comprising the amino acid sequence of SEQ ID NOs: 3-5, 7-9, 12, 15-19, 22, 24, 27-30, 37, 67 or 74, or polynulceotides encoding the Foxp3 peptides for manufacturing an immunogenic composition for regulating immunosuppression. Alternatively, the present invention also relates to Foxp3 peptides selected from peptides comprising the amino acid sequence of SEQ ID NOs: 3-5, 7-9, 12, 15-19, 22, 24, 27-30, 37, 67 or 74 or polynulceotides encoding the Foxp3 peptides, for regulating immunosuppression.

Herein, regulating immunosupression indicates that the administration of the peptides, polynucleotides, exosomes, APCs or CTLs of the present invention causes any kind of change in vivo. In some embodiments, the change caused by the present peptides, polynucleotides, exosomes, APCs and CTLs is a decrease in the level of the immunosuppressing state (suppression or counteracting of immunosuppression), namely, induction of anti-immunosuppression. Therefore, the present invention also provides a method of inducing anti-immunosuppression, said method comprises steps of administering the present peptides, polynucleotides, exosomes, APCs or CTLs to a subject in need thereof.

In general, anti-immunosuppression includes immune responses such as follows:

induction of cytotoxic lymphocytes against T-regs expressing Foxp3, induction of antibodies that recognize T-regs expressing Foxp3, and induction of anti-Tregs cytokine production.

Therefore, when a certain protein induces any one of these immune responses upon inoculation into an animal, the protein is decided to have anti-immunosupression inducing effect. The induction of the anti-immunosupression by a protein can be detected by observing in vivo or in vitro response of the host immune system against the protein.

For example, a method for detecting the induction (i.e., activation) of cytotoxic T lymphocytes is well known. Specifically, it is known that a foreign substance that enters the living body is presented to T cells and B cells by the action of antigen presenting cells (APCs). T cells that respond to the antigen presented by APC in antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to a T cell by APC, and detecting the induction (i.e., proliferation, IFN-gamma production, and Cytotoxic activity) of CTL. Furthermore, APCs have the effect of activating CD4+ T cells, CD8+ T cells, macrophages, eosinophils and NK cells. Since CD4+ T cells are also important in anti-tumor immunity, the anti-tumor immunity inducing action of the peptide can be evaluated using the activation effect of these cells as indicators.

A method for evaluating the action to induce CTLs using dendritic cells (DCs) as APC is well known in the art. According to this method, a test peptide is initially contacted with DC and then this DC is contacted with T cells. Detection of T cells having cytotoxic effects against cells expressing (i.e., presenting on an HLA molecule) the peptide of interest after the contact with DC shows that the test peptide has an activity of inducing the cytotoxic T cells. Activity of CTL against T-regs can be detected, for example, using the lysis of $^{51}$Cr-labeled tumor cells as the indicator. Alternatively, the method of evaluating the degree of T-regs damage using $^{3}$H-thymidine uptake activity or LDH (lactose dehydrogenase)-release as the indicator is also well known and can be used in the present invention.

Apart from DC, peripheral blood mononuclear cells (PBMCs) can also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The test peptides confirmed to possess CTL inducing activity by these methods are peptides having a DC activation effect and subsequent CTL inducing activity. Therefore, Foxp3 peptides that induce CTL against tumor cells are useful as vaccines against T-regs. Furthermore, APC that acquired the ability to induce CTL against T-regs by the contact with the Foxp3 peptides are also useful as vaccines against T-regs.

Furthermore, CTL that acquired cytotoxicity due to the presentation of the peptide antigens by APC can be also be used as vaccines against T-regs. Such regulating methods for T-regs using immunity due to APC and CTL are referred to as cellular immunotherapy and are encompassed by the present invention.

Generally, when using a polypeptide for cellular immunotherapy, efficiency of CTL-induction is known to be increased by combining a plurality of peptides having different structures and contacting them with DC. Therefore, when stimulating DC with protein fragments, it is advantageous to use a mixture of multiple types of fragments.

Alternatively, the induction of anti-immunosuppression by a peptide can be confirmed by observing the induction of antibody production against T-regs. For example, when antibodies against a peptide are induced in an individual, e.g., a human patient, a laboratory animal, immunized with the peptide, and when T-reg cells are suppressed by those antibodies, the peptide can be determined to have an ability to induce anti-immunosuppression.

Anti-immunosuppression is induced by administering the vaccine of this invention, and the induction enables dissolution of immunosuppression. Such effects can be statistically significant. For example, in observation, at a significance level of 5% or less, wherein the regulating effect of a vaccine against T-regs is compared to a control without vaccine administration. For example, Student's t-test, the Mann-Whitney U-test or ANOVA can be used for statistical analyses.

When using APC or CTL as the vaccine of this invention, T-regs can be regulated (i.e., suppressed), for example, by the ex vivo method. More specifically, PBMCs of the subject receiving treatment or prevention are collected, the cells are contacted with the polypeptide ex vivo, and following the induction of APC or CTL, the cells can be administered to the subject. APC can be also induced by introducing a vector encoding the polypeptide into PBMCs ex vivo. APC or CTL induced in vitro can be cloned prior to administration. By cloning and growing cells having high activity of damaging target cells, cellular immunotherapy can be performed more effectively. Furthermore, APC and CTL isolated in this manner can be used for cellular immunotherapy not only against individuals from whom the cells are derived, but also against similar types of diseases in other individuals.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The following examples are presented to illustrate the present invention and to assist one of ordinary skill in making and using the same. The examples are not intended in any way to otherwise limit the scope of the invention.

EXAMPLES

Materials and Methods

Cell Lines

A24LCL cells (HLA-A24/24), T2 cells (HLA-A02/02), human B-lymphoblastoid cells, 293T and COST were purchased from ATCC.

Candidate Selection of Peptide Derived from Foxp3

9-mer and 10-mer peptides derived from Foxp3 that bind to HLA-A*2402 and HLA-A*0201 molecule were predicted by binding prediction software "BIMAS" (http://bimas.dcrt.nih.gov/cgi-bin/molbio/ken_parker_comboform), the algorithms were described by Parker K C, et al. ((1994) J Immunol.; 152(1):163-75.) and Kuzushima K, et al. ((2001) Blood.; 98(6):1872-81.). These peptides were synthesized by Sigma (Sapporo, Japan) according to the standard solid phase synthesis method and purified by reversed phase HPLC. The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce CTL responses against peptides presented on HLA. DCs were generated in vitro as described elsewhere (Horiguchi S. et al. Cancer Res. 59:2950-6). Specifically, peripheral blood mononuclear cells (PBMCs) isolated from normal volunteer (HLA-A*2402 and/or HLA-A*0201) with Ficoll-Plaque (Pharmacia) solution were separated by adherence to plastic tissue culture dish (Becton Dickinson) so as to enrich them for the monocyte fraction. The monocyte-enriched population was cultured in the presence of 1000 U/ml of GM-CSF (R&D System) and 1000 U/ml of IL-4 (R&D System) in AIM-V medium (Invitrogen) containing 2% heat-inactivated autologous serum (AS). After 7 days in the culture, the cytokine-generated DCs were pulsed with 20 mcg/ml of the synthesized peptides in the presence of 3 mcg/ml of beta2-microglobulin for 4 hrs at 20 degrees C. in AIM-V medium. These peptide-pulsed DCs were then inactivated with mitomycin C (MMC) (30 mcg/ml for 30 mins) and mixed at a 1:20 ratio with autologous CD8+ T cells, obtained by positive selection with CD8 Positive Isolation Kit (Dynal). These cultures were set up in 48-well plates (Corning); each well contained $1.5\times10^4$ peptide-pulsed DCs, $3\times10^5$ CD8+ T cells and 10 ng/ml of IL-7 (R&D System) in 0.5 ml of AIM-V/2% AS. Three days later, these cultures were supplemented with IL-2 (CHIRON) to a final concentration of 20 IU/ml. On day 7 and 14, the T cells were further restimulated with the peptide-pulsed autologous DCs. The DCs were prepared each time through the same procedure described above. CTL activity was tested against peptide-pulsed A24LCL cells or T2 cells after the 3rd round of peptide stimulation on day 21.

CTL Expansion Procedure

CTLs were expanded in culture using a similar method as reported by Riddell, et al. (Walter et al., N Engl J Med 333 (16): 1038-44, 1995; Riddell et al., Nat Med 2(2): 216-23, 1996 February). A total of $5\times10^4$ CTLs were resuspended in 25 ml of AIM-V/5% AS with 2 kinds of human B-lymphoblastoid cell lines, inactivated with MMC, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS containing 30 IU/ml of IL-2 on days 5, 8 and 11.

Specific CTL Activity

To examine the specific CTL activity, IFN-gamma ELISPOT assay and IFN-gamma ELISA were performed. Briefly, peptide-pulsed A24-LCL, T2 cell ($1\times10^4$/well) or the cells endogenously expressing Foxp3 and HLA molecule was prepared as a stimulator cells. Cultured CTL lines in 48 wells were used as a responder cells. IFN-gamma ELISPOT assay and IFN-gamma ELISA were performed under manufacture procedure.

Immunogenicity of Epitope Peptides in BALB/c Mice

For priming the peptide-specific CTLs, immunization was given using 100 mcl vaccine mixture, which contains 50 mcl HLA-A24 restricted peptide and 50 mcl IFA per mouse. The vaccine was injected s.c. into the right flank of mice for the first immunization on day 0 and in the left flank for the second on the day 7. On day 14, splenocytes from vaccinated mice were used as the responder cells, and RLmale1 cells pulsed with or without peptides were used as the stimulator cells for IFN-gamma ELISPOT assay.

In Vivo Antitumor Effects

4T1 cells ($1\times10^5$ per mouse) were injected s.c. into the right flank of BALB/c mice on day 0. Vaccination was done on days 3 and 10 using hFoxp3-252 (KLSAMQAHL: SEQ ID NO: 17) or mFoxp3-252 (KLGAMQAHL: SEQ ID NO: 88) IFA-conjugated peptides.

Assay for Affinity of Foxp3-9-252 Substitutions to HLA Molecule

IFN-gamma ELISA assay was performed to examine the affinity of substituted peptide to HLA-A2 molecule. CTLs induced with Foxp3-9-252-WT (KLSAMQAHL: SEQ ID NO: 17) peptide were used as responder cells and T2 cells were prepared as stimulator cells by incubation with Foxp3-9-252-WT, Foxp3-9-252-9V (KLSAMQAHV: SEQ ID NO: 95) and HIV-A02 (SLYNTYATL) peptide at 37 degree Celsius for 2 hours. Peptide pulse to T2 cells were performed with wide range concentration ($10\text{-}10^{-4}$ mcg/ml) of each peptide.

Results

Prediction of HLA-A24 and HLA-A2 Binding Peptides Derived from Foxp3

Tables 1, 2 and 3 show HLA-A*2402 binding peptides or HLA-A*0201 binding peptides of the Foxp3 protein in the order of score of prediction high binding affinity. In total, 60 peptides with potential HLA-A24 binding activity and 26 peptides with potential HLA-A2 binding activity were selected.

TABLE 1

HLA-A2402 binding 9mer peptides derived from Foxp3

| | Start Position | Sequence | Score | SEQ ID NO |
|---|---|---|---|---|
| Foxp3-A24-9mer | 363 | IYHWFTRMF | 100 | 3 |
| | 207 | VFEEPEDFL | 36 | 4 |
| | 332 | KFHNMRPPF | 20 | 5 |
| | 323 | EFLHNMDYF | 15 | 6 |
| | 366 | WFTRMFAFF | 12 | 7 |
| | 337 | RPPFTYATL | 12 | 8 |
| | 190 | SYPLLANGV | 10.8 | 9 |
| | 27 | RAAPKASDL | 9.6 | 39 |
| | 238 | MVQSLEQQL | 8.64 | 40 |
| | 87 | GPLPHLQAL | 8.64 | 41 |
| | 252 | KLSAMQAHL | 8 | 17 |
| | 8 | KPSAPSLAL | 8 | 42 |
| | 352 | EAPEKQRTL | 7.2 | 43 |
| | 240 | QSLEQQLVL | 7.2 | 44 |
| | 245 | QLVLEKEKL | 6.6 | 45 |
| | 403 | GAVWTVDEL | 6.6 | 46 |
| | 185 | AVPQSSYPL | 6 | 47 |
| | 28 | AAPKASDLL | 6 | 48 |
| | 141 | FSLKARPGL | 6 | 49 |
| | 383 | NAIRHNLSL | 6 | 50 |
| | 186 | VPQSSYPLL | 6 | 51 |
| | 343 | ATLIRWAIL | 6 | 52 |
| | 200 | KWPGCEKVF | 6 | 53 |
| | 68 | QLQLPTLPL | 6 | 54 |
| | 341 | TYATLIRWA | 6 | 55 |
| | 115 | TPVLQVHPL | 6 | 56 |
| | 61 | LNPMPPSQL | 6 | 57 |
| | 159 | EWVSREPAL | 6 | 58 |
| | 175 | SAPRKDSTL | 6 | 59 |
| | 234 | LQREMVQSL | 5.76 | 60 |
| | 304 | SLFAVRRHL | 5.6 | 61 |
| | 359 | TLNEIYHWF | 5.04 | 62 |

Start position indicates the number of amino acid from the N-terminus of Foxp3.

Binding score is derived from "BIMAS" described in Materials and Methods.

TABLE 2

HLA-A2402 binding 10mer peptides derived from Foxp3

| | Start Position | Sequence | Score | SEQ ID NO |
|---|---|---|---|---|
| Foxp3-A24-10mer | 341 | TYATLIRWAI | 70 | 10 |
| | 140 | VFSLKARPGL | 20 | 11 |
| | 114 | RTPVLQVHPL | 12 | 12 |

TABLE 2-continued

| HLA-A2402 binding 10mer peptides derived from Foxp3 | | | |
|---|---|---|---|
| Start Position | Sequence | Score | SEQ ID NO |
| 27 | RAAPkASDLL | 9.6 | 63 |
| 206 | KVFEePEDFL | 9.6 | 64 |
| 402 | KGAVwTVDEL | 8.8 | 65 |
| 237 | EMVQsLEQQL | 8.64 | 66 |
| 87 | GPLPhLQALL | 8.64 | 67 |
| 303 | DSLFaVRRHL | 8.4 | 68 |
| 358 | RTLNeIYHWF | 8.4 | 69 |
| 5 | RPGKpSAPSL | 8 | 70 |
| 382 | KNAIrHNLSL | 8 | 71 |
| 190 | SYPLlANGVC | 7.5 | 72 |
| 86 | LGPLpHLQAL | 7.2 | 73 |
| 60 | SLNPmPPSQL | 7.2 | 74 |
| 184 | SAVPqSSYPL | 7.2 | 75 |
| 62 | NPMPpSQLQL | 7.2 | 76 |
| 233 | LLQReMVQSL | 7.2 | 77 |
| 244 | QQLVlEKEKL | 6.6 | 78 |
| 185 | AVPQsSYPLL | 6 | 79 |
| 149 | LPPGiNVASL | 6 | 80 |
| 296 | SGPReAPDSL | 6 | 81 |
| 77 | VMVApSGARL | 6 | 82 |
| 159 | EWVSrEPALL | 6 | 83 |
| 67 | SQLQIPTLPL | 6 | 84 |
| 316 | HGNStFPEFL | 6 | 85 |
| 380 | TWKNaIRHNL | 5.6 | 86 |
| 363 | IYHWfTRMFA | 5 | 87 |

Start position indicates the number of amino acid from the N-terminus of Foxp3.

Binding score is derived from “BIMAS” described in Materials and Methods.

TABLE 3

| HLA-A0201 binding peptides derived from Foxp3 | | | | |
|---|---|---|---|---|
| | Start Position | Sequence | Score | SEQ ID NO |
| Foxp3-A2-9mer | 388 | NLSLHKCFV | 382.536 | 13 |
| | 95 | LLQDRPHFM | 190.448 | 14 |
| | 390 | SLHKCFVRV | 132.149 | 15 |
| | 69 | LQLPTLPLV | 102.018 | 16 |
| | 252 | KLSAMQAHL | 74.768 | 17 |

TABLE 3-continued

| HLA-A0201 binding peptides derived from Foxp3 | | | | |
|---|---|---|---|---|
| | Start Position | Sequence | Score | SEQ ID NO |
| | 68 | QLQLPTLPL | 21.362 | 18 |
| | 304 | SLFAVRRHL | 15.808 | 19 |
| | 239 | VQSLEQQLV | 11.988 | 20 |
| | 245 | QLVLEKEKL | 10.468 | 21 |
| Foxp3-A2-10mer | 359 | TLNEIYHWFT | 1260.32 | 22 |
| | 206 | KVFEEPEDFL | 267.467 | 23 |
| | 263 | KMALTKASSV | 175.812 | 24 |

TABLE 3-continued

HLA-A0201 binding peptides derived from Foxp3

| Start Position | Sequence | Score | SEQ ID NO |
|---|---|---|---|
| 70 | QLPTLPLVMV | 159.97 | 25 |
| 68 | QLQLPTLPLV | 159.97 | 26 |
| 94 | ALLQDRPHFM | 101.099 | 27 |
| 233 | LLQREMVQSL | 83.527 | 28 |
| 152 | GINVASLEWV | 59.279 | 29 |
| 77 | VMVAPSGARL | 26.228 | 30 |
| 60 | SLNPMPPSQL | 21.362 | 31 |
| 299 | REAPDSLFAV | 18.041 | 32 |
| 252 | KLSAMQAHLA | 17.388 | 33 |
| 102 | FMHQLSTVDA | 16.505 | 34 |
| 223 | LLDEKGRAQC | 13.851 | 35 |
| 344 | TLIRWAILEA | 11.426 | 36 |
| 246 | LVLEKEKLSA | 11.21 | 37 |
| 238 | MVQSLEQQLV | 10.346 | 38 |

Start position indicates the number of amino acid from the N-terminus of Foxp3.

Binding score is derived from "BIMAS" described in Materials and Methods.

Stimulation of the T Cells Using the Predicted Peptides Restricted with HLA-A2402

CTLs for the peptides derived from Foxp3 protein were generated according to the method described in the "Materials and Methods", supra. Resulting CTLs showing detectable specific CTL activity by IFN-gamma ELISPOT assay are shown in FIG. 1A and FIG. 1B. In FIG. 1A, the cells in the well number #2 and 7 stimulated with Foxp3-A24-9-363, #1 and #6 with Foxp3-A24-9-366, #5 with Foxp3-A24-9-190, #7 with Foxp3-A24-10-87, and with Foxp3-A24-10-60 showed potent IFN-gamma production compared with the control. In FIG. 1B, the cells in the well number #4 stimulated with Foxp3-A24-9-207, #6 with Foxp3-A24-9-332, #6 with Foxp3-A24-9-337, and #1 with Foxp3-A24-10-114 showed potent IFN-gamma production compared with the control.

Stimulation of the T Cells Using the Predicted Peptides Restricted with HLA-A0201

Resulting CTLs showing detectable specific CTL activity were shown in FIG. 2A, FIG. 2B and FIG. 2C when performed by IFN-gamma ELISPOT assay. In FIG. 2A, the cells in the well number #2 stimulated with Foxp3-A2-9-390, #2 with Foxp3-A2-9-69, #6 with Foxp3-A2-9-252, #4 with Foxp3-A2-10-359, #7 with Foxp3-A2-263, and #2 and #5 with Foxp3-A2-10-94 showed potent IFN-gamma production compared with the control. In FIG. 2B, the cells in the all well stimulated with Foxp3-A2-10-233, the well number #6 and #7 with Foxp3-A2-10-152, #5 with Foxp3-A2-10-77, #1 with Foxp3-A2-10-246 and with Foxp3-A2-10-94 showed potent IFN-gamma production compared with the control. In FIG. 2C, the cells in the well number #1, 2, 4, 5, 7, 9, 11 and 12 stimulated with Foxp3-A2-9-390, the well number #5 and #11 with Foxp3-A2-9-304, the well number #7 with Foxp3-A2-9-68 and the well number #12 with Foxp3-A2-9-252 showed potent IFN-gamma production compared with the control.

Establishment for CTL Lines from Foxp3 Specific Peptides

These cells in the positive wells were expanded and performed IFN-gamma ELISA assay. In FIG. 3A, B, C, CTL lines stimulated with Foxp3-A02-9-390 (SEQ ID NO: 15) showed potent IFN-gamma production compared with the control. In FIG. 3D, CTL lines stimulated with Foxp3-A02-9-252 (SEQ ID NO: 17) showed potent IFN-gamma production compared with the control. In FIG. 3E, CTL lines stimulated with Foxp3-A24-10-60 (SEQ ID NO: 75) showed potent IFN-gamma production compared with the control. In FIG. 3F, CTL lines stimulated with Foxp3-A02-10-94 (SEQ ID NO: 27) showed potent IFN-gamma production compared with the control. In FIG. 3G, CTL lines stimulated with Foxp3-A24-10-87 (SEQ ID NO: 68) showed potent IFN-gamma production compared with the control.

Specific CTL Activity Against the Target Cells Endogenously Expressing Foxp3 and HLA-A*2402 or HLA-A*0201

The established CTL clone raised against these peptides were examined for their ability to recognize the target cells endogenously expressing Foxp3 and HLA-A*24 or 02. Specific CTL activity against 293T transfected both full length of Foxp3 gene and HLA-A*24 or 02 molecule, which is specific model for the target cells endogenously express Foxp3 and HLA-A*24 or 02, was tested using the CTL lines raised by Foxp3-A02-9-390 (SEQ ID NO: 15) and Foxp3-A02-9-252 (SEQ ID NO: 17) as effector cells. In FIG. 4A and FIG. 4B, CTL lines raised by Foxp3-A02-9-390 (SEQ ID NO: 15) and Foxp3-A02-9-252 (SEQ ID NO: 17) showed high specific CTL activity against 293T that transfected both Foxp3 and HLA-A02. In FIG. 4C, CTL lines raised by Foxp3-A02-9-252 (SEQ ID NO: 17) showed high specific CTL activity against 293T that transfected both Foxp3 and HLA-A24. On the other hand, it did not show significant specific CTL activity against controls. It clearly demonstrated that Foxp3-A02-9-390 and Foxp3-A02-9-252 was naturally expressed to the target cell surface with HLA-A02 and/or 24 molecule and recognized CTL. Furthermore, these peptides were epitope peptides, which can utilize vaccine targeting Foxp3 expressed T-regs.

Immunogenicity of Foxp3-A24-9-252 Peptide in BALB/c Mice

Figure 5:
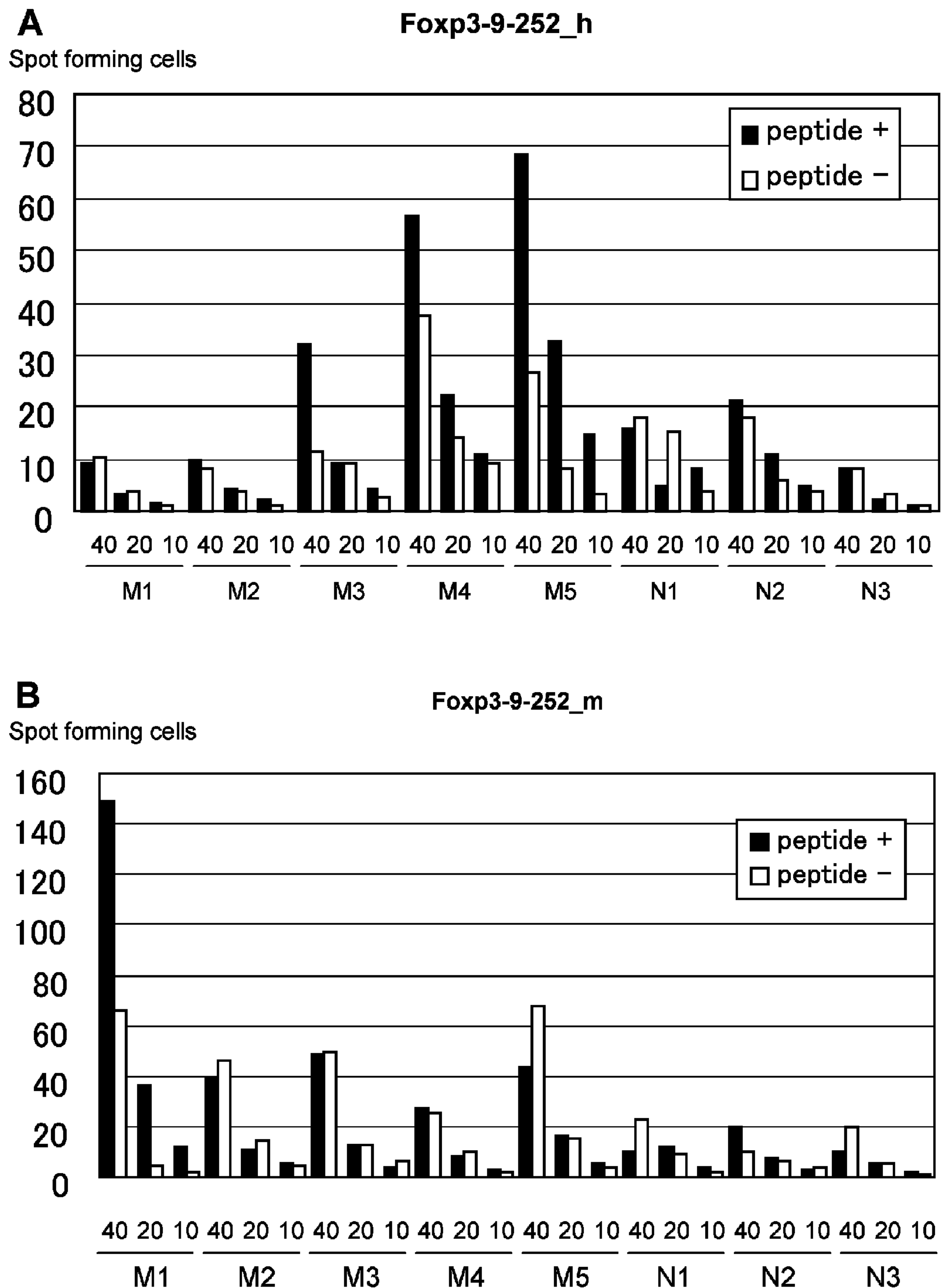
FIG. 5 shows in vivo analysis of immunogenicity of Foxp3-252_h and Foxp3-252_m peptide. IFA-conjugated peptide or IFA only were injected s.c. into BALB/c mice on day 0 and 7. On day 14, splenocytes of vaccinated mice were harvested and used as responder cells. $1\times10^4$ RLmale1 cells pulsed corresponding peptide (solid square), or no peptide (open square) were used as stimulator cells for IFN-gamma ELISPOT assay. Vaccination using Foxp3-252_h (A) and Foxp3-252_m (B) were performed into five mice (M1-M5) and IFA without any peptide injection were performed into three mice (N1-N3) as control in each assay.

To evaluate the immunogenicity of Foxp3-9-252 peptide for BALB/c mice, immunization with human Foxp3-9-252 peptide (Foxp3-252_h; KLSAMQAHL)(SEQ ID NO: 17) and mouse Foxp3-9-252 peptide (Foxp3-252_m; KLGAMQAHL) (SEQ ID NO: 89) were performed, respectively. After second injection of peptide, peptide specific CTL activity was determined by IFN-gamma ELISPOT assay (FIG. 5).

From splenocytes harvested from peptide-vaccinated mice, potent IFN-gamma production was detected in the well which co-cultured with corresponding peptide pulsed stimulator cells without showing IFN-gamma production in the control wells. In FIG. 5A, Foxp3-252_h peptide specific CTL response was detected from three of five mice (M3, M4 and M5) but not in control mice (N1~N3) which vaccinated IFA only. In FIG. 5B, Foxp3-252_m peptide specific CTL response was detected from one of five mice (M1) but not in control mice (N1~N3) which vaccinated IFA only. These data indicated that peptide vaccination of each Foxp3-252_h or Foxp3-252_m peptide can induces CTLs against peptide-pulsed target cells in vivo.

Antitumor Effects of Vaccination of Foxp3 Epitope Peptide

Figure 6:
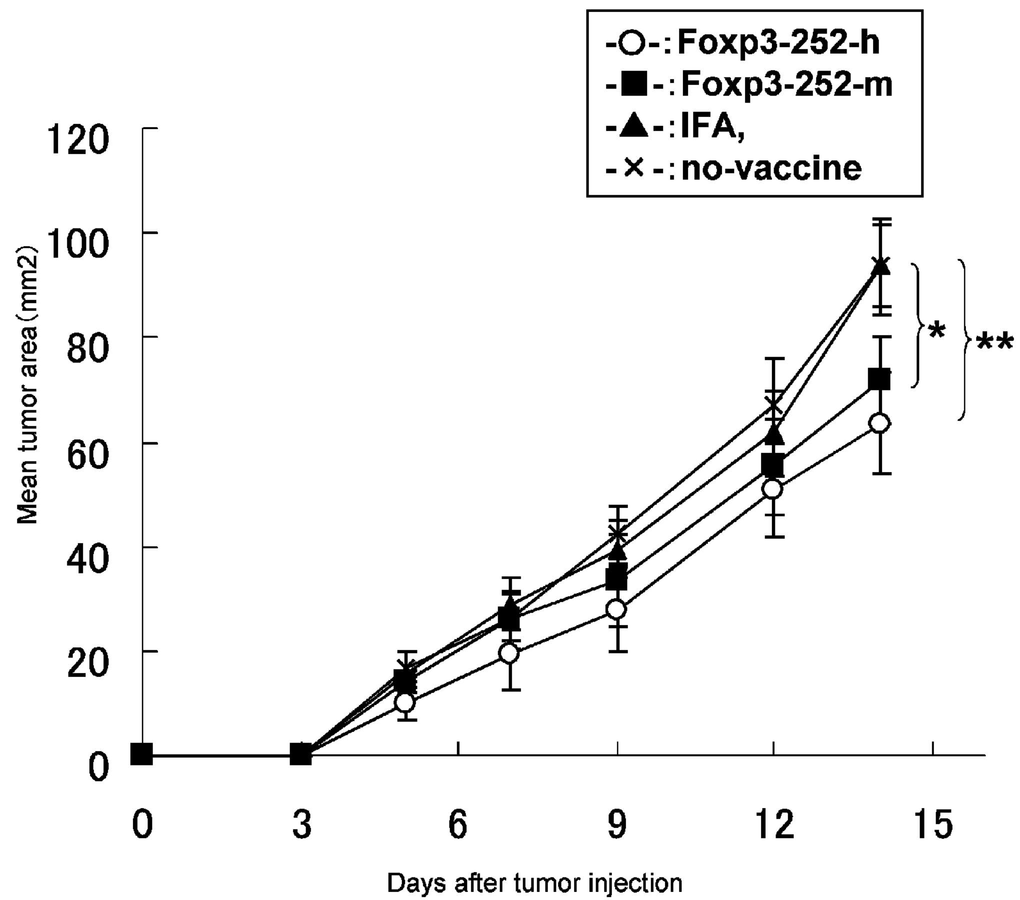
FIG. 6 shows in vivo antitumor effects of vaccination using Foxp3 epitope peptide. $1\times10^5$ 4T1 breast cancer cell lines were injected into BALB/c mice on day 0. IFA-conjugated with Foxp3-252_h (-open circle-), Foxp3-252_m (-solid square-), no peptide (-solid triangle-) was injected on day 3 and 10. As control of normal tumor growth, non-vaccinated mice (-x-) were also prepared in this assay. Significant difference of tumor growth suppression was observed with the vaccination of Foxp3 epitope peptide. *, P<0.01; **, P<0.005.

To examine the antitumor effects with peptide vaccination targeted Foxp3, in vivo therapeutic setting was attempted by using 4T1 tumor cells and BALB/c mice. The 4T1 breast cancer cells were injected s.c. into BALB/c mice on day 0, and then vaccination was done on these mice 3 and 10 days after the tumor challenge. As a result, tumor growth apparently reduced in BALB/c mice vaccinated Foxp3-252_h or Foxp3-252_m peptides compared with it in mice as control (FIG. 6). Considering to statistical analysis, it showed a significant difference with suppression of tumor growth in the mice with vaccination using Foxp3 epitope peptides.

Amino Acid Substitution of Foxp3 Epitope Peptide

In aforementioned results, Foxp3-9-252 peptide (SEQ ID NO 17) is identified as epitope peptide restricted with both HLA-A*2402 and HLA-A*0201. To enhance the immunogenicity of Foxp3-9-252 peptide, a single or a couple of amino acid(s) substitutions were selected to achieve higher binding affinity to HLA-A*2402 or HLA-A*0201 molecule than natural Foxp3-9-252 peptide; Foxp3-9-252-WT (KLSAMQAHL) (SEQ ID NO 17). Binding score of amino acid substitution in Foxp3-9-252 (SEQ ID NO 17) are derived from the BIMAS software. Table 4 shows amino acid sequences and binding score to HLA-A*2402 and 0201 molecule of substituted peptide from Foxp3-9-252. Binding score of peptide are derived from the BIMAS software. Six or nine kinds of substitutions, a total of fifteen peptides, which predicted to have higher binding affinity to HLA-A24 or HLA-A2 molecule than wild type were synthesized (Table 4).

TABLE 4

Binding score of amino acid substitution in Foxp3-9-252 (SEQ ID NO 17) to HLA-A*2402 or 0201 molecule

| | Peptide Name | Sequence | Binding Score | SEQ ID NO |
|---|---|---|---|---|
| A2402 | Foxp3-9-252 | KLSAMQAHL | 8.0 | 17 |
| | 2Y | KYSAMQAHL | 400.0 | 89 |
| | 2F | KFSAMQAHL | 40.0 | 90 |
| | Y9I | KYSAMQAHI | 100.0 | 91 |
| | 2Y9F | KYSAMQAHF | 200.0 | 92 |
| | 2F9I | KFSAMQAHI | 10.0 | 93 |
| | 2F9F | KFSAMQAHF | 20.0 | 94 |
| A0201 | WT | KLSAMQAHL | 74.8 | 17 |
| | 9V | KLSAMQAHV | 243.4 | 95 |
| | 3Y | KLYAMQAHL | 239.3 | 96 |
| | 3M | KLMAMQAHL | 276.6 | 97 |
| | 3L | KLLAMQAHL | 276.6 | 98 |
| | 3F | KLFAMQAHL | 276.6 | 99 |
| | 3Y9V | KLYAMQAHV | 779.0 | 100 |
| | 3M9V | KLMAMQAHV | 900.7 | 101 |
| | 3L9V | KLLAMQAHV | 900.7 | 102 |
| | 3F9V | KLFAMQAHV | 900.7 | 103 |

And then the present inventers examined whether peptide-pulsed stimulator cells using these substitutions were recognized by CTLs generated with Foxp3-9-252-WT peptide. In consequence, CTLs induced by the Foxp3-9-252-WT peptide produced IFN-gamma against Foxp3-9-252-9V (KLSAMQAHV) (SEQ ID NO 95) pulsed T2 cells, likewise Foxp3-9-252-WT peptide pulsed T2 cells (FIG. 7A). Since no IFN-gamma production were detected from CTLs against stimulator cells without any peptide-pulse, it indicated that CTLs generated with Foxp3-9-252-WT peptide can recognize the presentation of Foxp3-9-252-9V peptide on HLA-A2 molecule as well as Foxp3-9-252-WT.

Furthermore, to evaluate whether Foxp3-9-252-9V peptide had higher affinity to HLA-A2 molecule than Foxp3-9-252-WT peptide, CTL activity was determined using the stimulator cells pulsed with these peptides in wide range concentration ($10\text{-}10^{-4}$ mcg/ml). As a result, similar IFN-gamma was produced from CTLs co-cultured with stimulator cells which pulsed with Foxp3-9-252-WT or Foxp3-9-252-9V peptide, respectively (FIG. 7B). From these data, it was shown that the presentation of Foxp3-9-252-9V peptide on HLA-A*0201 molecule could be recognized by CTLs established with Foxp3-9-252-WT peptide.

On the other hand, the present inventers attempted the induction of CTLs using all substitutions restricted HLA-A*0201 including Foxp3-9-252-9V peptide. As a result, CTLs were induced by stimulation with Foxp3-9-252-3M (KLMAMQAHL) (SEQ ID NO 97), Foxp3-9-252-3L (KLLAMQAHL) (SEQ ID NO 98) or Foxp3-9-252-9V peptide (FIG. 7C). The cells in the well number 3 and 7 stimulated with Foxp3-A02-9-252-3M, well number 7 with Foxp3-A02-9-252-3L, and well number 8 with Foxp3-A02-9-252-9V showed peptide-dependent IFN-gamma production compared with the control. After CTL line induced by stimulation with Foxp3-9-252-9V was established by in vitro expansion, the CTL activity was determined by using stimulator cells pulsed with Foxp3-9-252-WT or Foxp3-9-252-9V peptide. Consequently, CTLs induced by stimulation with Foxp3-9-252-9V recognized stimulator cells pulsed Foxp3-9-252-WT peptide as equal to that pulsed Foxp3-9-252-9V peptide (FIG. 7D). These results strongly exhibited that Foxp3-9-252-9V peptide could induce Foxp3 specific CTLs as well as Foxp3-9-252-WT peptide.

Homology Analysis of the Antigen Peptides

The CTLs stimulated with
FOXp3-A24-9-363 (SEQ ID NO 3),
FOXp3-A24-9-366 (SEQ ID NO 7),
FOXp3-A24-9-190 (SEQ ID NO 9),
FOXp3-A24-9-207 (SEQ ID NO 4),
FOXp3-A24-9-332 (SEQ ID NO 5),
FOXp3-A24-9-337 (SEQ ID NO 8),
FOXp3-A24-10-114 (SEQ ID NO 12),
FOXp3-A2-9-390 (SEQ ID NO 15),
FOXp3-A2-9-69 (SEQ ID NO 16),
FOXp3-A2-9-252 (SEQ ID NO 17),
FOXp3-A2-10-359 (SEQ ID NO 22),
FOXp3-A2-10-263 (SEQ ID NO 24),
FOXp3-A2-10-94 (SEQ ID NO 27),
FOXp3-A2-10-233 (SEQ ID NO 28),
FOXp3-A2-10-152 (SEQ ID NO 29),
FOXp3-A2-10-77 (SEQ ID NO 30),
FOXp3-A2-10-246 (SEQ ID NO 37),
FOXp3-A2-9-68 (SEQ ID NO 18),
FOXp3-A2-9-304 (SEQ ID NO 19)
Foxp3-A24-10-87 (SEQ ID NO 67) and
Foxp3-A24-10-60 (SEQ ID NO 74) showed significant and specific CTL activity.

This Might Mean that the Sequence of
FOXp3-A24-9-363 (SEQ ID NO 3),
FOXp3-A24-9-366 (SEQ ID NO 7),
FOXp3-A24-9-190 (SEQ ID NO 9),
FOXp3-A24-9-207 (SEQ ID NO 4),
FOXp3-A24-9-332 (SEQ ID NO 5),
FOXp3-A24-9-337 (SEQ ID NO 8),
FOXp3-A24-10-114 (SEQ ID NO 12),
FOXp3-A2-9-390 (SEQ ID NO 15),
FOXp3-A2-9-69 (SEQ ID NO 16),
FOXp3-A2-9-252 (SEQ ID NO 17),
FOXp3-A2-10-359 (SEQ ID NO 22),
FOXp3-A2-10-263 (SEQ ID NO 24),
FOXp3-A2-10-94 (SEQ ID NO 27),
FOXp3-A2-10-233 (SEQ ID NO 28),
FOXp3-A2-10-152 (SEQ ID NO 29),
FOXp3-A2-10-77 (SEQ ID NO 30),
FOXp3-A2-10-246 (SEQ ID NO 37),
FOXp3-A2-9-68 (SEQ ID NO 18),
FOXp3-A2-9-304 (SEQ ID NO 19)
Foxp3-A24-10-87 (SEQ ID NO 67) and
Foxp3-A24-10-60 (SEQ ID NO 74) is homologous to the peptides derived from other molecules, which are known to sensitize human immune system. To exclude this possibility, homology analysis was performed with the peptide sequences as queries using BLAST algorithm (http://www.ncbi.nlm.nih.gov/blast/blast.cgi) and revealed no sequence with significant homology.

These results indicate that the sequence of
FOXp3-A24-9-363 (SEQ ID NO 3),
FOXp3-A24-9-366 (SEQ ID NO 7),
FOXp3-A24-9-190 (SEQ ID NO 9),
FOXp3-A24-9-207 (SEQ ID NO 4),
FOXp3-A24-9-332 (SEQ ID NO 5),
FOXp3-A24-9-337 (SEQ ID NO 8),
FOXp3-A24-10-114 (SEQ ID NO 12),
FOXp3-A2-9-390 (SEQ ID NO 15),
FOXp3-A2-9-69 (SEQ ID NO 16),
FOXp3-A2-9-252 (SEQ ID NO 17),
FOXp3-A2-10-359 (SEQ ID NO 22),
FOXp3-A2-10-263 (SEQ ID NO 24),
FOXp3-A2-10-94 (SEQ ID NO 27),
FOXp3-A2-10-233 (SEQ ID NO 28),
FOXp3-A2-10-152 (SEQ ID NO 29),
FOXp3-A2-10-77 (SEQ ID NO 30),
FOXp3-A2-10-246 (SEQ ID NO 37),
FOXp3-A2-9-68 (SEQ ID NO 18),
FOXp3-A2-9-304 (SEQ ID NO 19)
Foxp3-A24-10-87 (SEQ ID NO 67) and
Foxp3-A24-10-60 (SEQ ID NO 74) is unique and there is little possibility, to our best knowledge, to raise unintended immunologic response to any unrelated molecule.

In conclusion, Foxp3 is an antigen useful in targeting T-reg cells, and vaccines using these epitope peptides can be useful for immunotherapy.

Discussion

From the data of FIG. 6, vaccination of each hFoxp3-252 and mFoxp3-252 peptide could induce epitope specific CTLs in vivo. It indicated that both Foxp3 epitope peptides could induce CTLs against the target cells expressed Foxp3 and corresponding major histocompatibility complex molecule. In other word, it is suggested that these CTLs might recognize to regulatory T lymphocytes (T-regs). To evaluate this hypothesis, in vivo antitumor effects of the vaccination with these Foxp3 epitope peptides were examined by using BALB/c mice. It showed obviously anti-tumor effects in the mice vaccinated with hFoxp3-252 and mFoxp3-252 peptide, respectively. These results strongly indicated that tumor growth could be inhibited by suppression of T-regs into the local tumor microenvironment, even without vaccination using any TAA epitope peptides. The present inventers consider that CTLs against tumor cells are induced when tumor exist inside of the body, however, T-regs are also induced by some immune suppressive factors from tumor cells and inhibit the function of antitumor effector cells. Since vaccination using Foxp3 epitope peptide could cancel the immunosuppressive situation by means of killing or suppression T-regs, antitumor effects were shown without vaccination TAA epitope peptide or stimulation whole immune system using strong adjuvant.

By the way, vaccination of hFoxp3-252 peptide (KLSAMQAHL) (SEQ ID NO 17) could induce CTLs and antitumor effects superior to mFoxp3-252 peptide (KLGAMQAHL) (SEQ ID NO 88) in FIG. 5 and FIG. 6. From these results, it was considered that vaccination of hFoxp3-252 peptide might avoid immunologic tolerance efficiently compared with vaccination of mFoxp3-252 peptide. In other word, since amino acid sequence of hFoxp3-252 is different from that of mFoxp3-252 in position 3, hFoxp3-252 peptide is considered "not self-antigen" in vivo and could induce CTLs against T-regs efficiently.

In conclusion, it is indicated that Foxp3 could serve as novel targets for cancer immunotherapy. Furthermore these results strongly support that vaccination using Foxp3 epitope peptide could suppress the function of T-regs, and should be available to cancer immunotherapy for many types of cancer cells.

The invention claimed is:

1. An isolated peptide having cytotoxic T cell inducibility, wherein the peptide consists of the amino acid sequence of SEQ ID NO: 17.

2. An isolated peptide having cytotoxic T cell inducibility, wherein the peptide consists of the amino acid sequence of SEQ ID NO: 95, 97 or 98.

3. A pharmaceutical composition comprising a peptide having cytotoxic T cell inducibility, wherein the peptide consists of the amino acid sequence of SEQ ID NO: 17, 95, 97, or 98.

4. The pharmaceutical composition of claim 3, which is a vaccine.

5. The pharmaceutical composition of claim 4, further comprising a second peptide which has the ability to induce cytotoxic T cells against cancerous cells or a polynucleotide encoding the second peptide.

* * * * *

SEQUENCE LISTING

```
<160> NUMBER OF SEQ ID NOS: 103

<210> SEQ ID NO 1
<211> LENGTH: 1869
<212> TYPE: DNA
<213> ORGANISM: Homo sapiens
<220> FEATURE:
<221> NAME/KEY: CDS
<222> LOCATION: (189)..(1484)

<400> SEQUENCE: 1

gcacacactc atcgaaaaaa atttggatta ttagaagaga gaggtctgcg gcttccacac      60

cgtacagcgt ggtttttctt ctcggtataa aagcaaagtt gtttttgata cgtgacagtt     120
```

```
tcccacaagc caggctgatc cttttctgtc agtccacttc accaagcctg cccttggaca    180

aggacccg atg ccc aac ccc agg cct ggc aag ccc tcg gcc cct tcc ttg     230
         Met Pro Asn Pro Arg Pro Gly Lys Pro Ser Ala Pro Ser Leu
         1               5                   10

gcc ctt ggc cca tcc cca gga gcc tcg ccc agc tgg agg gct gca ccc      278
Ala Leu Gly Pro Ser Pro Gly Ala Ser Pro Ser Trp Arg Ala Ala Pro
15                  20                  25                  30

aaa gcc tca gac ctg ctg ggg gcc cgg ggc cca ggg gga acc ttc cag      326
Lys Ala Ser Asp Leu Leu Gly Ala Arg Gly Pro Gly Gly Thr Phe Gln
                35                  40                  45

ggc cga gat ctt cga ggc ggg gcc cat gcc tcc tct tct tcc ttg aac      374
Gly Arg Asp Leu Arg Gly Gly Ala His Ala Ser Ser Ser Ser Leu Asn
            50                  55                  60

ccc atg cca cca tcg cag ctg cag ctg ccc aca ctg ccc cta gtc atg      422
Pro Met Pro Pro Ser Gln Leu Gln Leu Pro Thr Leu Pro Leu Val Met
        65                  70                  75

gtg gca ccc tcc ggg gca cgg ctg ggc ccc ttg ccc cac tta cag gca      470
Val Ala Pro Ser Gly Ala Arg Leu Gly Pro Leu Pro His Leu Gln Ala
    80                  85                  90

ctc ctc cag gac agg cca cat ttc atg cac cag ctc tca acg gtg gat      518
Leu Leu Gln Asp Arg Pro His Phe Met His Gln Leu Ser Thr Val Asp
95                  100                 105                 110

gcc cac gcc cgg acc cct gtg ctg cag gtg cac ccc ctg gag agc cca      566
Ala His Ala Arg Thr Pro Val Leu Gln Val His Pro Leu Glu Ser Pro
                115                 120                 125

gcc atg atc agc ctc aca cca ccc acc acc gcc act ggg gtc ttc tcc      614
Ala Met Ile Ser Leu Thr Pro Pro Thr Thr Ala Thr Gly Val Phe Ser
            130                 135                 140

ctc aag gcc cgg cct ggc ctc cca cct ggg atc aac gtg gcc agc ctg      662
Leu Lys Ala Arg Pro Gly Leu Pro Pro Gly Ile Asn Val Ala Ser Leu
        145                 150                 155

gaa tgg gtg tcc agg gag ccg gca ctg ctc tgc acc ttc cca aat ccc      710
Glu Trp Val Ser Arg Glu Pro Ala Leu Leu Cys Thr Phe Pro Asn Pro
    160                 165                 170

agt gca ccc agg aag gac agc acc ctt tcg gct gtg ccc cag agc tcc      758
Ser Ala Pro Arg Lys Asp Ser Thr Leu Ser Ala Val Pro Gln Ser Ser
175                 180                 185                 190

tac cca ctg ctg gca aat ggt gtc tgc aag tgg ccc gga tgt gag aag      806
Tyr Pro Leu Leu Ala Asn Gly Val Cys Lys Trp Pro Gly Cys Glu Lys
                195                 200                 205

gtc ttc gaa gag cca gag gac ttc ctc aag cac tgc cag gcg gac cat      854
Val Phe Glu Glu Pro Glu Asp Phe Leu Lys His Cys Gln Ala Asp His
            210                 215                 220

ctt ctg gat gag aag ggc agg gca caa tgt ctc ctc cag aga gag atg      902
Leu Leu Asp Glu Lys Gly Arg Ala Gln Cys Leu Leu Gln Arg Glu Met
        225                 230                 235

gta cag tct ctg gag cag cag ctg gtg ctg gag aag gag aag ctg agt      950
Val Gln Ser Leu Glu Gln Gln Leu Val Leu Glu Lys Glu Lys Leu Ser
    240                 245                 250

gcc atg cag gcc cac ctg gct ggg aaa atg gca ctg acc aag gct tca      998
Ala Met Gln Ala His Leu Ala Gly Lys Met Ala Leu Thr Lys Ala Ser
255                 260                 265                 270

tct gtg gca tca tcc gac aag ggc tcc tgc tgc atc gta gct gct ggc     1046
Ser Val Ala Ser Ser Asp Lys Gly Ser Cys Cys Ile Val Ala Ala Gly
                275                 280                 285

agc caa ggc cct gtc gtc cca gcc tgg tct ggc ccc cgg gag gcc cct     1094
Ser Gln Gly Pro Val Val Pro Ala Trp Ser Gly Pro Arg Glu Ala Pro
            290                 295                 300

gac agc ctg ttt gct gtc cgg agg cac ctg tgg ggt agc cat gga aac     1142
```

```
Asp Ser Leu Phe Ala Val Arg Arg His Leu Trp Gly Ser His Gly Asn
        305                 310                 315

agc aca ttc cca gag ttc ctc cac aac atg gac tac ttc aag ttc cac     1190
Ser Thr Phe Pro Glu Phe Leu His Asn Met Asp Tyr Phe Lys Phe His
    320                 325                 330

aac atg cga ccc cct ttc acc tac gcc acg ctc atc cgc tgg gcc atc     1238
Asn Met Arg Pro Pro Phe Thr Tyr Ala Thr Leu Ile Arg Trp Ala Ile
335                 340                 345                 350

ctg gag gct cca gag aag cag cgg aca ctc aat gag atc tac cac tgg     1286
Leu Glu Ala Pro Glu Lys Gln Arg Thr Leu Asn Glu Ile Tyr His Trp
                355                 360                 365

ttc aca cgc atg ttt gcc ttc ttc aga aac cat cct gcc acc tgg aag     1334
Phe Thr Arg Met Phe Ala Phe Phe Arg Asn His Pro Ala Thr Trp Lys
            370                 375                 380

aac gcc atc cgc cac aac ctg agt ctg cac aag tgc ttt gtg cgg gtg     1382
Asn Ala Ile Arg His Asn Leu Ser Leu His Lys Cys Phe Val Arg Val
        385                 390                 395

gag agc gag aag ggg gct gtg tgg acc gtg gat gag ctg gag ttc cgc     1430
Glu Ser Glu Lys Gly Ala Val Trp Thr Val Asp Glu Leu Glu Phe Arg
    400                 405                 410

aag aaa cgg agc cag agg ccc agc agg tgt tcc aac cct aca cct ggc     1478
Lys Lys Arg Ser Gln Arg Pro Ser Arg Cys Ser Asn Pro Thr Pro Gly
415                 420                 425                 430

ccc tga cctcaagatc aaggaaagga ggatggacga acaggggcca aactggtggg      1534
Pro
aggcagaggt ggtgggggca gggatgatag gccctggatg tgcccacagg gaccaagaag   1594

tgaggtttcc actgtcttgc ctgccagggc ccctgttccc ccgctggcag ccaccccctc   1654

ccccatcata tcctttgccc caaggctgct cagaggggcc ccggtcctgg ccccagcccc   1714

cacctccgcc ccagacacac cccccagtcg agccctgcag ccaaacagag ccttcacaac   1774

cagccacaca gagcctgcct cagctgctcg cacagattac ttcagggctg gaaaagtcac   1834

acagacacac aaaatgtcac aatcctgtcc ctcac                              1869


<210> SEQ ID NO 2
<211> LENGTH: 431
<212> TYPE: PRT
<213> ORGANISM: Homo sapiens

<400> SEQUENCE: 2

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140
```

```
Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430
```

<210> SEQ ID NO 3
<211> LENGTH: 9
<212> TYPE: PRT
<213> ORGANISM: Artificial
<220> FEATURE:
<223> OTHER INFORMATION: peptide vaccine

<400> SEQUENCE: 3

```
Ile Tyr His Trp Phe Thr Arg Met Phe
1               5
```

<210> SEQ ID NO 4
<211> LENGTH: 9
<212> TYPE: PRT
<213> ORGANISM: Artificial
<220> FEATURE:
<223> OTHER INFORMATION: peptide vaccine

<400> SEQUENCE: 4

```
Val Phe Glu Glu Pro Glu Asp Phe Leu
1               5
```

<210> SEQ ID NO 5
<211> LENGTH: 9
<212> TYPE: PRT
<213> ORGANISM: Artificial
<220> FEATURE:
<223> OTHER INFORMATION: peptide vaccine

<400> SEQUENCE: 5

Lys Phe His Asn Met Arg Pro Pro Phe
1               5

<210> SEQ ID NO 6
<211> LENGTH: 9
<212> TYPE: PRT
<213> ORGANISM: Artificial
<220> FEATURE:
<223> OTHER INFORMATION: peptide vaccine

<400> SEQUENCE: 6

Glu Phe Leu His Asn Met Asp Tyr Phe
1               5

<210> SEQ ID NO 7
<211> LENGTH: 9
<212> TYPE: PRT
<213> ORGANISM: Artificial
<220> FEATURE:
<223> OTHER INFORMATION: peptide vaccine

<400> SEQUENCE: 7

Trp Phe Thr Arg Met Phe Ala Phe Phe
1               5

<210> SEQ ID NO 8
<211> LENGTH: 9
<212> TYPE: PRT
<213> ORGANISM: Artificial
<220> FEATURE:
<223> OTHER INFORMATION: peptide vaccine

<400> SEQUENCE: 8

Arg Pro Pro Phe Thr Tyr Ala Thr Leu
1               5

<210> SEQ ID NO 9
<211> LENGTH: 9
<212> TYPE: PRT
<213> ORGANISM: Artificial
<220> FEATURE:
<223> OTHER INFORMATION: peptide vaccine

<400> SEQUENCE: 9

Ser Tyr Pro Leu Leu Ala Asn Gly Val
1               5

<210> SEQ ID NO 10
<211> LENGTH: 10
<212> TYPE: PRT
<213> ORGANISM: Artificial
<220> FEATURE:
<223> OTHER INFORMATION: peptide vaccine

<400> SEQUENCE: 10

Thr Tyr Ala Thr Leu Ile Arg Trp Ala Ile
1               5                   10

<210> SEQ ID NO 11

<211> LENGTH: 10
<212> TYPE: PRT
<213> ORGANISM: Artificial
<220> FEATURE:
<223> OTHER INFORMATION: peptide vaccine

<400> SEQUENCE: 11

Val Phe Ser Leu Lys Ala Arg Pro Gly Leu
1 5 10

<210> SEQ ID NO 12
<211> LENGTH: 10
<212> TYPE: PRT
<213> ORGANISM: Artificial
<220> FEATURE:
<223> OTHER INFORMATION: peptide vaccine

<400> SEQUENCE: 12

Arg Thr Pro Val Leu Gln Val His Pro Leu
1 5 10

<210> SEQ ID NO 13
<211> LENGTH: 9
<212> TYPE: PRT
<213> ORGANISM: Artificial
<220> FEATURE:
<223> OTHER INFORMATION: peptide vaccine

<400> SEQUENCE: 13

Asn Leu Ser Leu His Lys Cys Phe Val
1 5

<210> SEQ ID NO 14
<211> LENGTH: 9
<212> TYPE: PRT
<213> ORGANISM: Artificial
<220> FEATURE:
<223> OTHER INFORMATION: peptide vaccine

<400> SEQUENCE: 14

Leu Leu Gln Asp Arg Pro His Phe Met
1 5

<210> SEQ ID NO 15
<211> LENGTH: 9
<212> TYPE: PRT
<213> ORGANISM: Artificial
<220> FEATURE:
<223> OTHER INFORMATION: peptide vaccine

<400> SEQUENCE: 15

Ser Leu His Lys Cys Phe Val Arg Val
1 5

<210> SEQ ID NO 16
<211> LENGTH: 9
<212> TYPE: PRT
<213> ORGANISM: Artificial
<220> FEATURE:
<223> OTHER INFORMATION: peptide vaccine

<400> SEQUENCE: 16

Leu Gln Leu Pro Thr Leu Pro Leu Val
1 5

<210> SEQ ID NO 17
<211> LENGTH: 9
<212> TYPE: PRT

<213> ORGANISM: Artificial
<220> FEATURE:
<223> OTHER INFORMATION: peptide vaccine

<400> SEQUENCE: 17

Lys Leu Ser Ala Met Gln Ala His Leu
1 5

<210> SEQ ID NO 18
<211> LENGTH: 9
<212> TYPE: PRT
<213> ORGANISM: Artificial
<220> FEATURE:
<223> OTHER INFORMATION: peptide vaccine

<400> SEQUENCE: 18

Gln Leu Gln Leu Pro Thr Leu Pro Leu
1 5

<210> SEQ ID NO 19
<211> LENGTH: 9
<212> TYPE: PRT
<213> ORGANISM: Artificial
<220> FEATURE:
<223> OTHER INFORMATION: peptide vaccine

<400> SEQUENCE: 19

Ser Leu Phe Ala Val Arg Arg His Leu
1 5

<210> SEQ ID NO 20
<211> LENGTH: 9
<212> TYPE: PRT
<213> ORGANISM: Artificial
<220> FEATURE:
<223> OTHER INFORMATION: peptide vaccine

<400> SEQUENCE: 20

Val Gln Ser Leu Glu Gln Gln Leu Val
1 5

<210> SEQ ID NO 21
<211> LENGTH: 9
<212> TYPE: PRT
<213> ORGANISM: Artificial
<220> FEATURE:
<223> OTHER INFORMATION: peptide vaccine

<400> SEQUENCE: 21

Gln Leu Val Leu Glu Lys Glu Lys Leu
1 5

<210> SEQ ID NO 22
<211> LENGTH: 10
<212> TYPE: PRT
<213> ORGANISM: Artificial
<220> FEATURE:
<223> OTHER INFORMATION: peptide vaccine

<400> SEQUENCE: 22

Thr Leu Asn Glu Ile Tyr His Trp Phe Thr
1 5 10

<210> SEQ ID NO 23
<211> LENGTH: 10
<212> TYPE: PRT
<213> ORGANISM: Artificial
<220> FEATURE:

```
<223> OTHER INFORMATION: peptide vaccine

<400> SEQUENCE: 23

Lys Val Phe Glu Glu Pro Glu Asp Phe Leu
1               5                   10


<210> SEQ ID NO 24
<211> LENGTH: 10
<212> TYPE: PRT
<213> ORGANISM: Artificial
<220> FEATURE:
<223> OTHER INFORMATION: peptide vaccine

<400> SEQUENCE: 24

Lys Met Ala Leu Thr Lys Ala Ser Ser Val
1               5                   10


<210> SEQ ID NO 25
<211> LENGTH: 10
<212> TYPE: PRT
<213> ORGANISM: Artificial
<220> FEATURE:
<223> OTHER INFORMATION: peptide vaccine

<400> SEQUENCE: 25

Gln Leu Pro Thr Leu Pro Leu Val Met Val
1               5                   10


<210> SEQ ID NO 26
<211> LENGTH: 10
<212> TYPE: PRT
<213> ORGANISM: Artificial
<220> FEATURE:
<223> OTHER INFORMATION: peptide vaccine

<400> SEQUENCE: 26

Gln Leu Gln Leu Pro Thr Leu Pro Leu Val
1               5                   10


<210> SEQ ID NO 27
<211> LENGTH: 10
<212> TYPE: PRT
<213> ORGANISM: Artificial
<220> FEATURE:
<223> OTHER INFORMATION: peptide vaccine

<400> SEQUENCE: 27

Ala Leu Leu Gln Asp Arg Pro His Phe Met
1               5                   10


<210> SEQ ID NO 28
<211> LENGTH: 10
<212> TYPE: PRT
<213> ORGANISM: Artificial
<220> FEATURE:
<223> OTHER INFORMATION: peptide vaccine

<400> SEQUENCE: 28

Leu Leu Gln Arg Glu Met Val Gln Ser Leu
1               5                   10


<210> SEQ ID NO 29
<211> LENGTH: 10
<212> TYPE: PRT
<213> ORGANISM: Artificial
<220> FEATURE:
<223> OTHER INFORMATION: peptide vaccine
```

<400> SEQUENCE: 29

Gly Ile Asn Val Ala Ser Leu Glu Trp Val
1 5 10

<210> SEQ ID NO 30
<211> LENGTH: 10
<212> TYPE: PRT
<213> ORGANISM: Artificial
<220> FEATURE:
<223> OTHER INFORMATION: peptide vaccine

<400> SEQUENCE: 30

Val Met Val Ala Pro Ser Gly Ala Arg Leu
1 5 10

<210> SEQ ID NO 31
<211> LENGTH: 10
<212> TYPE: PRT
<213> ORGANISM: Artificial
<220> FEATURE:
<223> OTHER INFORMATION: peptide vaccine

<400> SEQUENCE: 31

Ser Leu Asn Pro Met Pro Pro Ser Gln Leu
1 5 10

<210> SEQ ID NO 32
<211> LENGTH: 10
<212> TYPE: PRT
<213> ORGANISM: Artificial
<220> FEATURE:
<223> OTHER INFORMATION: peptide vaccine

<400> SEQUENCE: 32

Arg Glu Ala Pro Asp Ser Leu Phe Ala Val
1 5 10

<210> SEQ ID NO 33
<211> LENGTH: 10
<212> TYPE: PRT
<213> ORGANISM: Artificial
<220> FEATURE:
<223> OTHER INFORMATION: peptide vaccine

<400> SEQUENCE: 33

Lys Leu Ser Ala Met Gln Ala His Leu Ala
1 5 10

<210> SEQ ID NO 34
<211> LENGTH: 10
<212> TYPE: PRT
<213> ORGANISM: Artificial
<220> FEATURE:
<223> OTHER INFORMATION: peptide vaccine

<400> SEQUENCE: 34

Phe Met His Gln Leu Ser Thr Val Asp Ala
1 5 10

<210> SEQ ID NO 35
<211> LENGTH: 10
<212> TYPE: PRT
<213> ORGANISM: Artificial
<220> FEATURE:
<223> OTHER INFORMATION: peptide vaccine

<400> SEQUENCE: 35

```
Leu Leu Asp Glu Lys Gly Arg Ala Gln Cys
1               5                   10


<210> SEQ ID NO 36
<211> LENGTH: 10
<212> TYPE: PRT
<213> ORGANISM: Artificial
<220> FEATURE:
<223> OTHER INFORMATION: peptide vaccine

<400> SEQUENCE: 36

Thr Leu Ile Arg Trp Ala Ile Leu Glu Ala
1               5                   10


<210> SEQ ID NO 37
<211> LENGTH: 10
<212> TYPE: PRT
<213> ORGANISM: Artificial
<220> FEATURE:
<223> OTHER INFORMATION: peptide vaccine

<400> SEQUENCE: 37

Leu Val Leu Glu Lys Glu Lys Leu Ser Ala
1               5                   10


<210> SEQ ID NO 38
<211> LENGTH: 10
<212> TYPE: PRT
<213> ORGANISM: Artificial
<220> FEATURE:
<223> OTHER INFORMATION: peptide vaccine

<400> SEQUENCE: 38

Met Val Gln Ser Leu Glu Gln Gln Leu Val
1               5                   10


<210> SEQ ID NO 39
<211> LENGTH: 9
<212> TYPE: PRT
<213> ORGANISM: Artificial
<220> FEATURE:
<223> OTHER INFORMATION: peptide

<400> SEQUENCE: 39

Arg Ala Ala Pro Lys Ala Ser Asp Leu
1               5


<210> SEQ ID NO 40
<211> LENGTH: 9
<212> TYPE: PRT
<213> ORGANISM: Artificial
<220> FEATURE:
<223> OTHER INFORMATION: peptide vaccine

<400> SEQUENCE: 40

Met Val Gln Ser Leu Glu Gln Gln Leu
1               5


<210> SEQ ID NO 41
<211> LENGTH: 9
<212> TYPE: PRT
<213> ORGANISM: Artificial
<220> FEATURE:
<223> OTHER INFORMATION: peptide vaccine

<400> SEQUENCE: 41

Gly Pro Leu Pro His Leu Gln Ala Leu
1               5
```

<210> SEQ ID NO 42
<211> LENGTH: 9
<212> TYPE: PRT
<213> ORGANISM: Artificial
<220> FEATURE:
<223> OTHER INFORMATION: peptide vaccine

<400> SEQUENCE: 42

Lys Pro Ser Ala Pro Ser Leu Ala Leu
1 5

<210> SEQ ID NO 43
<211> LENGTH: 9
<212> TYPE: PRT
<213> ORGANISM: Artificial
<220> FEATURE:
<223> OTHER INFORMATION: peptide vaccine

<400> SEQUENCE: 43

Glu Ala Pro Glu Lys Gln Arg Thr Leu
1 5

<210> SEQ ID NO 44
<211> LENGTH: 9
<212> TYPE: PRT
<213> ORGANISM: Artificial
<220> FEATURE:
<223> OTHER INFORMATION: peptide vaccine

<400> SEQUENCE: 44

Gln Ser Leu Glu Gln Gln Leu Val Leu
1 5

<210> SEQ ID NO 45
<211> LENGTH: 9
<212> TYPE: PRT
<213> ORGANISM: Artificial
<220> FEATURE:
<223> OTHER INFORMATION: peptide vaccine

<400> SEQUENCE: 45

Gln Leu Val Leu Glu Lys Glu Lys Leu
1 5

<210> SEQ ID NO 46
<211> LENGTH: 9
<212> TYPE: PRT
<213> ORGANISM: Artificial
<220> FEATURE:
<223> OTHER INFORMATION: peptide vaccine

<400> SEQUENCE: 46

Gly Ala Val Trp Thr Val Asp Glu Leu
1 5

<210> SEQ ID NO 47
<211> LENGTH: 9
<212> TYPE: PRT
<213> ORGANISM: Artificial
<220> FEATURE:
<223> OTHER INFORMATION: peptide vaccine

<400> SEQUENCE: 47

Ala Val Pro Gln Ser Ser Tyr Pro Leu
1 5

<210> SEQ ID NO 48
<211> LENGTH: 9
<212> TYPE: PRT
<213> ORGANISM: Artificial
<220> FEATURE:
<223> OTHER INFORMATION: peptide vaccine

<400> SEQUENCE: 48

Ala Ala Pro Lys Ala Ser Asp Leu Leu
1 5

<210> SEQ ID NO 49
<211> LENGTH: 9
<212> TYPE: PRT
<213> ORGANISM: Artificial
<220> FEATURE:
<223> OTHER INFORMATION: peptide vaccine

<400> SEQUENCE: 49

Phe Ser Leu Lys Ala Arg Pro Gly Leu
1 5

<210> SEQ ID NO 50
<211> LENGTH: 9
<212> TYPE: PRT
<213> ORGANISM: Artificial
<220> FEATURE:
<223> OTHER INFORMATION: peptide vaccine

<400> SEQUENCE: 50

Asn Ala Ile Arg His Asn Leu Ser Leu
1 5

<210> SEQ ID NO 51
<211> LENGTH: 9
<212> TYPE: PRT
<213> ORGANISM: Artificial
<220> FEATURE:
<223> OTHER INFORMATION: peptide vaccine

<400> SEQUENCE: 51

Val Pro Gln Ser Ser Tyr Pro Leu Leu
1 5

<210> SEQ ID NO 52
<211> LENGTH: 9
<212> TYPE: PRT
<213> ORGANISM: Artificial
<220> FEATURE:
<223> OTHER INFORMATION: peptide vaccine

<400> SEQUENCE: 52

Ala Thr Leu Ile Arg Trp Ala Ile Leu
1 5

<210> SEQ ID NO 53
<211> LENGTH: 9
<212> TYPE: PRT
<213> ORGANISM: Artificial
<220> FEATURE:
<223> OTHER INFORMATION: peptide vaccine

<400> SEQUENCE: 53

Lys Trp Pro Gly Cys Glu Lys Val Phe
1 5

<210> SEQ ID NO 54
<211> LENGTH: 9

<212> TYPE: PRT
<213> ORGANISM: Artificial
<220> FEATURE:
<223> OTHER INFORMATION: peptide vaccine

<400> SEQUENCE: 54

Gln Leu Gln Leu Pro Thr Leu Pro Leu
1               5

<210> SEQ ID NO 55
<211> LENGTH: 9
<212> TYPE: PRT
<213> ORGANISM: Artificial
<220> FEATURE:
<223> OTHER INFORMATION: peptide vaccine

<400> SEQUENCE: 55

Thr Tyr Ala Thr Leu Ile Arg Trp Ala
1               5

<210> SEQ ID NO 56
<211> LENGTH: 9
<212> TYPE: PRT
<213> ORGANISM: Artificial
<220> FEATURE:
<223> OTHER INFORMATION: peptide vaccine

<400> SEQUENCE: 56

Thr Pro Val Leu Gln Val His Pro Leu
1               5

<210> SEQ ID NO 57
<211> LENGTH: 9
<212> TYPE: PRT
<213> ORGANISM: Artificial
<220> FEATURE:
<223> OTHER INFORMATION: peptide vaccine

<400> SEQUENCE: 57

Leu Asn Pro Met Pro Pro Ser Gln Leu
1               5

<210> SEQ ID NO 58
<211> LENGTH: 9
<212> TYPE: PRT
<213> ORGANISM: Artificial
<220> FEATURE:
<223> OTHER INFORMATION: peptide vaccine

<400> SEQUENCE: 58

Glu Trp Val Ser Arg Glu Pro Ala Leu
1               5

<210> SEQ ID NO 59
<211> LENGTH: 9
<212> TYPE: PRT
<213> ORGANISM: Artificial
<220> FEATURE:
<223> OTHER INFORMATION: peptide vaccine

<400> SEQUENCE: 59

Ser Ala Pro Arg Lys Asp Ser Thr Leu
1               5

<210> SEQ ID NO 60
<211> LENGTH: 9
<212> TYPE: PRT
<213> ORGANISM: Artificial

<220> FEATURE:
<223> OTHER INFORMATION: peptide vaccine

<400> SEQUENCE: 60

Leu Gln Arg Glu Met Val Gln Ser Leu
1 5

<210> SEQ ID NO 61
<211> LENGTH: 9
<212> TYPE: PRT
<213> ORGANISM: Artificial
<220> FEATURE:
<223> OTHER INFORMATION: peptide vaccine

<400> SEQUENCE: 61

Ser Leu Phe Ala Val Arg Arg His Leu
1 5

<210> SEQ ID NO 62
<211> LENGTH: 9
<212> TYPE: PRT
<213> ORGANISM: Artificial
<220> FEATURE:
<223> OTHER INFORMATION: peptide vaccine

<400> SEQUENCE: 62

Thr Leu Asn Glu Ile Tyr His Trp Phe
1 5

<210> SEQ ID NO 63
<211> LENGTH: 10
<212> TYPE: PRT
<213> ORGANISM: Artificial
<220> FEATURE:
<223> OTHER INFORMATION: peptide vaccine

<400> SEQUENCE: 63

Arg Ala Ala Pro Lys Ala Ser Asp Leu Leu
1 5 10

<210> SEQ ID NO 64
<211> LENGTH: 10
<212> TYPE: PRT
<213> ORGANISM: Artificial
<220> FEATURE:
<223> OTHER INFORMATION: peptide vaccine

<400> SEQUENCE: 64

Lys Val Phe Glu Glu Pro Glu Asp Phe Leu
1 5 10

<210> SEQ ID NO 65
<211> LENGTH: 10
<212> TYPE: PRT
<213> ORGANISM: Artificial
<220> FEATURE:
<223> OTHER INFORMATION: peptide vaccine

<400> SEQUENCE: 65

Lys Gly Ala Val Trp Thr Val Asp Glu Leu
1 5 10

<210> SEQ ID NO 66
<211> LENGTH: 10
<212> TYPE: PRT
<213> ORGANISM: Artificial
<220> FEATURE:
<223> OTHER INFORMATION: peptide vaccine

<400> SEQUENCE: 66

Glu Met Val Gln Ser Leu Glu Gln Gln Leu
1 5 10

<210> SEQ ID NO 67
<211> LENGTH: 10
<212> TYPE: PRT
<213> ORGANISM: Artificial
<220> FEATURE:
<223> OTHER INFORMATION: peptide vaccine

<400> SEQUENCE: 67

Gly Pro Leu Pro His Leu Gln Ala Leu Leu
1 5 10

<210> SEQ ID NO 68
<211> LENGTH: 10
<212> TYPE: PRT
<213> ORGANISM: Artificial
<220> FEATURE:
<223> OTHER INFORMATION: peptide vaccine

<400> SEQUENCE: 68

Asp Ser Leu Phe Ala Val Arg Arg His Leu
1 5 10

<210> SEQ ID NO 69
<211> LENGTH: 10
<212> TYPE: PRT
<213> ORGANISM: Artificial
<220> FEATURE:
<223> OTHER INFORMATION: peptide vaccine

<400> SEQUENCE: 69

Arg Thr Leu Asn Glu Ile Tyr His Trp Phe
1 5 10

<210> SEQ ID NO 70
<211> LENGTH: 10
<212> TYPE: PRT
<213> ORGANISM: Artificial
<220> FEATURE:
<223> OTHER INFORMATION: peptide vaccine

<400> SEQUENCE: 70

Arg Pro Gly Lys Pro Ser Ala Pro Ser Leu
1 5 10

<210> SEQ ID NO 71
<211> LENGTH: 10
<212> TYPE: PRT
<213> ORGANISM: Artificial
<220> FEATURE:
<223> OTHER INFORMATION: peptide vaccine

<400> SEQUENCE: 71

Lys Asn Ala Ile Arg His Asn Leu Ser Leu
1 5 10

<210> SEQ ID NO 72
<211> LENGTH: 10
<212> TYPE: PRT
<213> ORGANISM: Artificial
<220> FEATURE:
<223> OTHER INFORMATION: peptide vaccine

<400> SEQUENCE: 72

```
Ser Tyr Pro Leu Leu Ala Asn Gly Val Cys
1               5                   10


<210> SEQ ID NO 73
<211> LENGTH: 10
<212> TYPE: PRT
<213> ORGANISM: Artificial
<220> FEATURE:
<223> OTHER INFORMATION: peptide vaccine

<400> SEQUENCE: 73

Leu Gly Pro Leu Pro His Leu Gln Ala Leu
1               5                   10


<210> SEQ ID NO 74
<211> LENGTH: 10
<212> TYPE: PRT
<213> ORGANISM: Artificial
<220> FEATURE:
<223> OTHER INFORMATION: peptide vaccine

<400> SEQUENCE: 74

Ser Leu Asn Pro Met Pro Pro Ser Gln Leu
1               5                   10


<210> SEQ ID NO 75
<211> LENGTH: 10
<212> TYPE: PRT
<213> ORGANISM: Artificial
<220> FEATURE:
<223> OTHER INFORMATION: peptide vaccine

<400> SEQUENCE: 75

Ser Ala Val Pro Gln Ser Ser Tyr Pro Leu
1               5                   10


<210> SEQ ID NO 76
<211> LENGTH: 10
<212> TYPE: PRT
<213> ORGANISM: Artificial
<220> FEATURE:
<223> OTHER INFORMATION: peptide vaccine

<400> SEQUENCE: 76

Asn Pro Met Pro Pro Ser Gln Leu Gln Leu
1               5                   10


<210> SEQ ID NO 77
<211> LENGTH: 10
<212> TYPE: PRT
<213> ORGANISM: Artificial
<220> FEATURE:
<223> OTHER INFORMATION: peptide vaccine

<400> SEQUENCE: 77

Leu Leu Gln Arg Glu Met Val Gln Ser Leu
1               5                   10


<210> SEQ ID NO 78
<211> LENGTH: 10
<212> TYPE: PRT
<213> ORGANISM: Artificial
<220> FEATURE:
<223> OTHER INFORMATION: peptide vaccine

<400> SEQUENCE: 78

Gln Gln Leu Val Leu Glu Lys Glu Lys Leu
```

1 5 10

<210> SEQ ID NO 79
<211> LENGTH: 10
<212> TYPE: PRT
<213> ORGANISM: Artificial
<220> FEATURE:
<223> OTHER INFORMATION: peptide vaccine

<400> SEQUENCE: 79

Ala Val Pro Gln Ser Ser Tyr Pro Leu Leu
1 5 10

<210> SEQ ID NO 80
<211> LENGTH: 10
<212> TYPE: PRT
<213> ORGANISM: Artificial
<220> FEATURE:
<223> OTHER INFORMATION: peptide vaccine

<400> SEQUENCE: 80

Leu Pro Pro Gly Ile Asn Val Ala Ser Leu
1 5 10

<210> SEQ ID NO 81
<211> LENGTH: 10
<212> TYPE: PRT
<213> ORGANISM: Artificial
<220> FEATURE:
<223> OTHER INFORMATION: peptide vaccine

<400> SEQUENCE: 81

Ser Gly Pro Arg Glu Ala Pro Asp Ser Leu
1 5 10

<210> SEQ ID NO 82
<211> LENGTH: 10
<212> TYPE: PRT
<213> ORGANISM: Artificial
<220> FEATURE:
<223> OTHER INFORMATION: peptide vaccine

<400> SEQUENCE: 82

Val Met Val Ala Pro Ser Gly Ala Arg Leu
1 5 10

<210> SEQ ID NO 83
<211> LENGTH: 10
<212> TYPE: PRT
<213> ORGANISM: Artificial
<220> FEATURE:
<223> OTHER INFORMATION: peptide vaccine

<400> SEQUENCE: 83

Glu Trp Val Ser Arg Glu Pro Ala Leu Leu
1 5 10

<210> SEQ ID NO 84
<211> LENGTH: 10
<212> TYPE: PRT
<213> ORGANISM: Artificial
<220> FEATURE:
<223> OTHER INFORMATION: peptide vaccine

<400> SEQUENCE: 84

Ser Gln Leu Gln Leu Pro Thr Leu Pro Leu
1 5 10

<210> SEQ ID NO 85
<211> LENGTH: 10
<212> TYPE: PRT
<213> ORGANISM: Artificial
<220> FEATURE:
<223> OTHER INFORMATION: peptide vaccine

<400> SEQUENCE: 85

His Gly Asn Ser Thr Phe Pro Glu Phe Leu
1 5 10

<210> SEQ ID NO 86
<211> LENGTH: 10
<212> TYPE: PRT
<213> ORGANISM: Artificial
<220> FEATURE:
<223> OTHER INFORMATION: peptide vaccine

<400> SEQUENCE: 86

Thr Trp Lys Asn Ala Ile Arg His Asn Leu
1 5 10

<210> SEQ ID NO 87
<211> LENGTH: 10
<212> TYPE: PRT
<213> ORGANISM: Artificial
<220> FEATURE:
<223> OTHER INFORMATION: peptide vaccine

<400> SEQUENCE: 87

Ile Tyr His Trp Phe Thr Arg Met Phe Ala
1 5 10

<210> SEQ ID NO 88
<211> LENGTH: 9
<212> TYPE: PRT
<213> ORGANISM: Artificial
<220> FEATURE:
<223> OTHER INFORMATION: peptide vaccine

<400> SEQUENCE: 88

Lys Leu Gly Ala Met Gln Ala His Leu
1 5

<210> SEQ ID NO 89
<211> LENGTH: 9
<212> TYPE: PRT
<213> ORGANISM: Artificial
<220> FEATURE:
<223> OTHER INFORMATION: peptide vaccine

<400> SEQUENCE: 89

Lys Tyr Ser Ala Met Gln Ala His Leu
1 5

<210> SEQ ID NO 90
<211> LENGTH: 9
<212> TYPE: PRT
<213> ORGANISM: Artificial
<220> FEATURE:
<223> OTHER INFORMATION: peptide vaccine

<400> SEQUENCE: 90

Lys Phe Ser Ala Met Gln Ala His Leu
1 5

<210> SEQ ID NO 91

<211> LENGTH: 9
<212> TYPE: PRT
<213> ORGANISM: Artificial
<220> FEATURE:
<223> OTHER INFORMATION: peptide vaccine

<400> SEQUENCE: 91

Lys Tyr Ser Ala Met Gln Ala His Ile
1 5

<210> SEQ ID NO 92
<211> LENGTH: 9
<212> TYPE: PRT
<213> ORGANISM: Artificial
<220> FEATURE:
<223> OTHER INFORMATION: peptide vaccine

<400> SEQUENCE: 92

Lys Tyr Ser Ala Met Gln Ala His Phe
1 5

<210> SEQ ID NO 93
<211> LENGTH: 9
<212> TYPE: PRT
<213> ORGANISM: Artificial
<220> FEATURE:
<223> OTHER INFORMATION: peptide vaccine

<400> SEQUENCE: 93

Lys Phe Ser Ala Met Gln Ala His Ile
1 5

<210> SEQ ID NO 94
<211> LENGTH: 9
<212> TYPE: PRT
<213> ORGANISM: Artificial
<220> FEATURE:
<223> OTHER INFORMATION: peptide vaccine

<400> SEQUENCE: 94

Lys Phe Ser Ala Met Gln Ala His Phe
1 5

<210> SEQ ID NO 95
<211> LENGTH: 9
<212> TYPE: PRT
<213> ORGANISM: Artificial
<220> FEATURE:
<223> OTHER INFORMATION: peptide vaccine

<400> SEQUENCE: 95

Lys Leu Ser Ala Met Gln Ala His Val
1 5

<210> SEQ ID NO 96
<211> LENGTH: 9
<212> TYPE: PRT
<213> ORGANISM: Artificial
<220> FEATURE:
<223> OTHER INFORMATION: peptide vaccine

<400> SEQUENCE: 96

Lys Leu Tyr Ala Met Gln Ala His Leu
1 5

<210> SEQ ID NO 97
<211> LENGTH: 9
<212> TYPE: PRT

<213> ORGANISM: Artificial
<220> FEATURE:
<223> OTHER INFORMATION: peptide vaccine

<400> SEQUENCE: 97

Lys Leu Met Ala Met Gln Ala His Leu
1               5

<210> SEQ ID NO 98
<211> LENGTH: 9
<212> TYPE: PRT
<213> ORGANISM: Artificial
<220> FEATURE:
<223> OTHER INFORMATION: peptide vaccine

<400> SEQUENCE: 98

Lys Leu Leu Ala Met Gln Ala His Leu
1               5

<210> SEQ ID NO 99
<211> LENGTH: 9
<212> TYPE: PRT
<213> ORGANISM: Artificial
<220> FEATURE:
<223> OTHER INFORMATION: peptide vaccine

<400> SEQUENCE: 99

Lys Leu Phe Ala Met Gln Ala His Leu
1               5

<210> SEQ ID NO 100
<211> LENGTH: 9
<212> TYPE: PRT
<213> ORGANISM: Artificial
<220> FEATURE:
<223> OTHER INFORMATION: peptide vaccine

<400> SEQUENCE: 100

Lys Leu Tyr Ala Met Gln Ala His Val
1               5

<210> SEQ ID NO 101
<211> LENGTH: 9
<212> TYPE: PRT
<213> ORGANISM: Artificial
<220> FEATURE:
<223> OTHER INFORMATION: peptide vaccine

<400> SEQUENCE: 101

Lys Leu Met Ala Met Gln Ala His Val
1               5

<210> SEQ ID NO 102
<211> LENGTH: 9
<212> TYPE: PRT
<213> ORGANISM: Artificial
<220> FEATURE:
<223> OTHER INFORMATION: peptide vaccine

<400> SEQUENCE: 102

Lys Leu Leu Ala Met Gln Ala His Val
1               5

<210> SEQ ID NO 103
<211> LENGTH: 9
<212> TYPE: PRT
<213> ORGANISM: Artificial
<220> FEATURE:

-continued

```
<223> OTHER INFORMATION: peptide vaccine

<400> SEQUENCE: 103

Lys Leu Phe Ala Met Gln Ala His Val
1               5
```